United States Patent
Natarajan et al.

(10) Patent No.: US 8,993,758 B2
(45) Date of Patent: Mar. 31, 2015

(54) SUBSTITUTED QUINOXALINES AND USES THEREOF

(75) Inventors: Amarnath Natarajan, Elkhorn, NE (US); Qianyi Chen, Shanghai (CN); Vashti C. Bryant, Cary, NC (US); Rajkumar Rajule, Omaha, NE (US)

(73) Assignees: Board of Regents of the University of Nebraska, Lincoln, NE (US); The Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 13/883,026

(22) PCT Filed: Nov. 22, 2011

(86) PCT No.: PCT/US2011/061848
§ 371 (c)(1),
(2), (4) Date: Jul. 11, 2013

(87) PCT Pub. No.: WO2012/071414
PCT Pub. Date: May 31, 2012

(65) Prior Publication Data
US 2013/0289041 A1    Oct. 31, 2013

Related U.S. Application Data

(60) Provisional application No. 61/416,001, filed on Nov. 22, 2010, provisional application No. 61/415,934, filed on Nov. 22, 2010.

(51) Int. Cl.
| | |
|---|---|
| *C07D 241/40* | (2006.01) |
| *C07D 241/42* | (2006.01) |
| *C07D 241/44* | (2006.01) |
| *C07D 405/04* | (2006.01) |
| *C07D 405/14* | (2006.01) |
| *C07D 409/14* | (2006.01) |
| *C07D 401/12* | (2006.01) |
| *C07D 401/14* | (2006.01) |
| *C07D 403/12* | (2006.01) |
| *C07D 471/04* | (2006.01) |

(52) U.S. Cl.
CPC ............ *C07D 241/42* (2013.01); *C07D 241/44* (2013.01); *C07D 405/04* (2013.01); *C07D 405/14* (2013.01); *C07D 409/14* (2013.01); *C07D 401/12* (2013.01); *C07D 401/14* (2013.01); *C07D 403/12* (2013.01); *C07D 471/04* (2013.01)
USPC ..................... 544/353; 546/268.1; 548/266.4; 548/560; 549/59; 549/505

(58) Field of Classification Search
CPC .................................................. C07D 241/40
USPC ............. 544/353; 546/268.1; 548/266.4, 560; 549/59, 505
See application file for complete search history.

(56) References Cited

U.S. PATENT DOCUMENTS

| | | | |
|---|---|---|---|
| 2004/0043247 A1 | 3/2004 | Lee et al. | |
| 2009/0163545 A1* | 6/2009 | Goldfarb | 514/312 |

FOREIGN PATENT DOCUMENTS

| | | |
|---|---|---|
| CN | 1590378 A | 3/2005 |
| CN | 1966500 A | 5/2007 |
| WO | WO-2005/007099 A2 | 1/2005 |
| WO | WO-2005/042513 A1 | 5/2005 |
| WO | WO-2006/047631 | 5/2006 |
| WO | WO-2008/083357 | 7/2008 |

OTHER PUBLICATIONS

Vippagunta, et al. Advanced Drug Delivery Reviews, 48, 2001, 18.*
Jordan, V. C. Nature Reviews: Drug Discovery, 2, 2003, 205.*
Hackam, et al. JAMA, 296(14), 2006, 1731-1732.*
Aggarwal, Nuclear factor-kappaB: the enemy within, Cancer Cell, 6(3):203-8 (2004).
Baldwin, The NF-kappa B and I kappa B proteins: new discoveries and insights, Annu. Rev. Immunol., 14:649-83 (1996).
Bjellqvist et al., The focusing positions of polypeptides in immobilized pH gradients can be predicted from their amino acid sequences, Electrophoresis, 14(10):1023-31 (1993).
Cascinu et al., COX-2 and NF-KB overexpression is common in pancreatic cancer but does not predict for COX-2 inhibitors activity in combination with gemcitabine and oxaliplatin, Am. J. Clin. Oncol., 30(5):526-30 (2007).
Chandler et al., Increased expression of NF-kappa B subunits in human pancreatic cancer cells, J. Surg. Res., 118(1):9-14 (2004).
Chen et al., 2,3-Substituted quinoxalin-6-amine analogs as antiproliferatives: a structure-activity relationship study, Bioorg. Med. Chem. Lett., 21(7):1929-32 (2011).
Cheng et al., Computation of the physio-chemical properties and data mining of large molecular collections, J. Comput. Chem., 23(1):172-83 (2002).
Chiang et al., Phosphorylation-dependent association of the G4-1/G5PR regulatory subunit with IKK? negatively modulates NF-?B activation through recruitment of protein phosphatase 5, Biochem. J., 433(1):187-96 (2011).
Clark et al., Progress in computational methods for the prediction of ADMET properties, Curr. Opin. Drug Discov. Devel., 5(3):382-90 (2002).

(Continued)

*Primary Examiner* — Douglas M Willis
(74) *Attorney, Agent, or Firm* — Marshall, Gerstein & Borun LLP

(57) ABSTRACT

Disclosed herein are compounds of formula (I) and methods of inhibiting IKKβ and the NF-κB signaling and mTOR pathways.

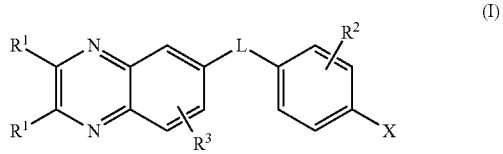

20 Claims, 10 Drawing Sheets

(56) References Cited

OTHER PUBLICATIONS

Conti et al., Induction of reIA(p65) and I kappa B alpha subunit expression during differentiation of human peripheral blood monocytes to macrophages, Cell Growth Differ., 8(4):435-42 (1997).
Darzynkiewicz et al., Cytometry of cyclin proteins, Cytometry, 25(1):1-13 (1996).
De Ritis et al., An enzymic test for the diagnosis of viral hepatitis; the transaminase serum activities, Clin. Chim. Acta., 2(1):70-4 (1957).
Delhase et al., Positive and negative regulation of IkappaB kinase activity through IKKbeta subunit phosphorylation, Science, 284(5412):309-13 (1999).
Druker et al., Effects of a selective inhibitor of the Abl tyrosine kinase on the growth of Bcr-Abl positive cells, Nat. Med., 2(5):561-6 (1996).
Farrow et al., Inflammation and the development of pancreatic cancer, Surg. Oncol., 10(4):153-69 (2002).
Fujioka et al., Function of nuclear factor kappaB in pancreatic cancer metastasis, Clin. Cancer Res., 9(1):346-54 (2003).
Gilmore, Introduction to NF-kappaB: players, pathways, perspectives, Oncogene, 25(51):6680-4 (2006).
Hacker et al., Regulation and function of IKK and IKK—related kinases, Sci STKE, 2006(357):re13 (2006).
Higuchi et al. (eds.), Pro-drugs as Novel Drug Delivery Systems, vol. 14, ACS Symposium Series (1975).
International Preliminary Report on Patentability from corresponding international application No. PCT/US11/61848, May 22, 2013.
International Search Report and Written Opinion from corresponding international applicaiton No. PCT/US11/61848, mailing date Jun. 27, 2012.
Kong et al., Downregulation of nuclear factor-kappaB p65 subunit by small interfering RNA synergizes with gemcitabine to inhibit the growth of pancreatic cancer, Cancer Lett., 291(1):90-8 (2010).
Lee et al., IKK beta suppression of TSC1 links inflammation and tumor angiogenesis via the mTOR pathway, Cell, 130(3):440-55 (2007).
Lipinski et al., Experimental and computational approaches to estimate solubility and permeability in drug discovery and development settings, Adv. Drug Deliv. Rev., 46(1-3):3-26 (2001).
Mattson et al., NF-kappaB in neuronal plasticity and neurodegenerative disorders, J. Clin. Invest., 107(3):247-54 (2001).
Mercurio et al., IKK-1 and IKK-2: cytokine-activated IkappaB kinases essential for NF-kappaB activation, Science, 278(5339):860-6 (1997).
Miyamoto et al., Enhanced I kappa B alpha degradation is responsible for constitutive NF-kappa B activity in mature murine B-cell lines, Mol. Cell Biol., 14(5):3276-82 (1994).
Morikane et al., Organ-specific pancreatic tumor growth properties and tumor immunity, Cancer Immunol. Immunother., 47(5):287-96 (1999).
Pan et al., Nuclear factor—kappaB p65/reIA silencing induces apoptosis and increases gemcitabine effectiveness in a subset of pancreatic cancer cells, Clin. Cancer Res., 14(24):8143-51 (2008).
Roche (ed.), Bioreversible Carriers in Drug Design, American Pharmaceutical Association and Pergamon Press (1987).
Salvesen et al., Caspase activation—stepping on the gas or releasing the brakes? Lessons from humans and flies, Oncogene, 23(16):2774-84 (2004).
Sen et al., Inducibility of kappa immunoglobulin enhancer-binding protein Nf-kappa B by a posttranslational mechanism, Cell, 47(6):921-8 (1986).
van Diest et al., Prognostic value of proliferation in invasive breast cancer: a review, J. Clin. Pathol., 57(7):675-81 (2004).
Wang et al., The nuclear factor-kappa B RelA transcription factor is constitutively activated in human pancreatic adenocarcinoma cells, Clin. Cancer Res., 5(1):119-27 (1999).
Weichert et al., High expression of RelA/p65 is associated with activation of nuclear factor-kappaB-dependent signaling in pancreatic cancer and marks a patient population with poor prognosis, Br. J. Cancer, 97(4):523-30 (2007).
Weidner, Current pathologic methods for measuring intratumoral microvessel density within breast carcinoma and other solid tumors, Breast Cancer Res. Treat., 36(2):169-80 (1995).
Zandi et al., Direct phosphorylation of IkappaB by IKKalpha and IKKbeta: discrimination between free and NF-kappaB-bound substrate, Science, 281(5381):1360-3 (1998).

* cited by examiner

SUBSTITUTED QUINOXALINES AND USES THEREOF

CROSS REFERENCE TO RELATED APPLICATIONS

This application claims the benefit of U.S. Provisional Application No. 61/416,001, filed Nov. 22, 2010, and U.S. Provisional Application No. 61/415,934, filed Nov. 22, 2010, each of which is incorporated by reference in its entirety.

STATEMENT OF U.S. GOVERNMENT SUPPORT

This invention was made with U.S. government support under Grant No. R01 CA127239, awarded by the National Institutes of Health. The U.S. government has certain rights in the invention.

BACKGROUND

Since its discovery 25 years ago, NF-κB has been shown to regulate the expression of over 200 immune, growth and inflammation genes. NF-κB is constitutively active in proliferating T cells, B cells, thymocytes, monocytes and astrocytes. The clinically silent onset of PC has been attributed to the upregulation of pro-inflammatory pathways such as NF-κB. NF-κB is constitutively active in most tumor cell lines and many tumor tissues derived from patients, but not in normal tissues. A similar observation was made in PC cell lines and pancreatic adenocarcinoma which showed constitutively activated RelA (p65 subunit of NF-κB), but not in normal pancreatic tissues or immortalized/non-tumorigenic pancreatic epithelial cells. Studies also showed that PC cell lines had increased levels of NF-κB subunits compared to non-malignant proliferating intestinal cells. These preclinical observations extend to PC patients: (i) High expression of RelA (NF-κB subunit p65) was observed in 64% of histologically or cytologically verified locally advanced unresectable and/or metastatic PC patients and (ii) this correlates with increased expression of NF-κB target genes and poor prognosis in this patient subgroup. Downregulation of NF-κB (RelA) using siRNA sensitizes a subset of PC cells and pancreatic tumors in nude mice to gemcitabine. Inhibiting constitutive NF-κB activity suppressed growth, angiogenesis and metastasis of PC. These observations suggest that NF-κB driven pro-inflammatory pathways lead to a subset of PC's and modulating the NF-κB activity is a viable therapeutic strategy for this subgroup.

The activity of IκB kinase β (IKKβ) is regulated by multiple phosphorylation events. IKKβ, like other kinases has an activation loop. Phosphorylation of two serine residues on the loop leads to the activation of IKKβ. IKKβ also has a stretch of serine residues at the C-terminus and IKKβ activation leads to auto-phosphorylation of the C-terminus serine residues. Unlike phosphorylation of the activation loop, phosphorylation of the C-terminal residues dampens kinase activity. Therefore, phosphorylation of the C-terminal serine residues not only makes IKKβ activation transient but also provides docking sites for phosphatases to dephosphorylate the serine residues on the activation loop. This suggests that IKKβ could exist in at least four distinct states as defined by its phosphorylation status and the kinase activity. The activation loop phosphorylated form of IKKβ is found in about 50% of surgical tumor specimens and in about 10% of normal tissues. Therefore, knowledge regarding the phosphorylation status of IKKβ is important from a biomarker and therapeutic development perspective. The lack of antibodies specific to the various states of IKKβ makes this a challenging problem.

A need exists for IKKβ inhibitors and methods of treating IKKβ-mediated disorders.

SUMMARY

Disclosed herein are compounds of formula (I):

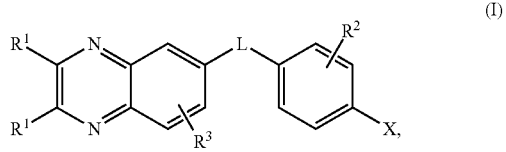

wherein each $R^1$ is independently heteroaryl, aryl, or alkyl; L is selected from —NHC(O)NH—, —NH—SO$_2$—, —NHC(O)CH$_2$—, —NHC(S)NH—,

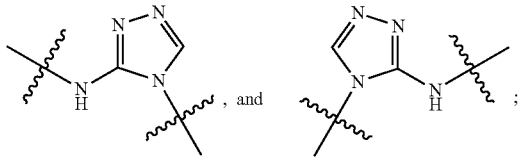 [SMILES: *Nc1nncn1* ; *Nc1nncn1*]

X is halo, alkyl, alkoxy, aryl, CO$_2$alkyl, COalkyl, or haloalkyl; $R^2$ is H, alkyl, alkoxy, CO$_2$alkyl, COalkyl, or haloalkyl; and $R^3$ is H, alkyl, or alkoxy; or a salt, hydrate, or solvate thereof. In some cases, at least one $R^1$ is furanyl, and in more specific cases, each $R^1$ is furanyl. In some cases, at least one $R^1$ is thiophenyl, and in more specific cases, each $R^1$ is thiophenyl. In some cases, at least one $R^1$ is phenyl, and in more specific cases, each $R^1$ is phenyl. In some cases, at least one $R^1$ is pyridyl, and in more specific cases, each $R^1$ is pyridyl. In some cases, at least one $R^1$ is alkyl, and in more specific cases, each $R^1$ is alkyl, and in even more specific cases, the alkyl is selected from methyl, ethyl, propyl, or isopropyl. In various cases, L is —NHC(O)NH—. In various cases, L is —NH—SO$_2$—. In various cases, L is —NHC(O)CH$_2$—. In various cases, L is —NHC(S)NH—. In various cases, L is

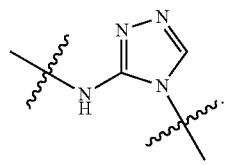 [SMILES: *Nc1nncn1*]

In various cases, L is

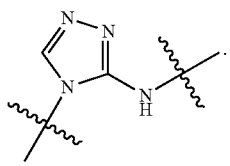 [SMILES: *Nc1nncn1*]

In some cases, X is halo, and in more specific cases is Br. In some cases, X is alkyl, and in more specific cases is methyl, ethyl, propyl, or isopropyl. In some cases, X is alkoxyl, and in more specific cases is methoxyl, ethoxyl, propoxyl, or isopropoxyl, or even more specific cases, is methoxy or ethoxy. In some cases, X is CO₂alkyl, and in more specific cases is CO₂CH₃ or CO₂CH₂CH₃. In some cases, X is COalkyl, and in more specific cases is COCH₃ or COCH₂CH₃. In some cases, X is haloalkyl, and in more specific cases is CF₃, CHF₂, CH₂F, CCl₃, CHCl₂, CH₂Cl, CBr₃, CHBr₂, or CH₂Br. In various cases, R² is H. In various cases, R² is alkyl, and in more specific cases is methyl, ethyl, propyl, or isopropyl. In various cases, R² is CO₂alkyl, and in more specific cases is CO₂CH₃ or CO₂CH₂CH₃. In various cases, R² is haloalkyl, and in more specific cases is CF₃, CHF₂, CH₂F, CCl₃, CHCl₂, CH₂Cl, CBr₃, CHBr₂, or CH₂Br. In some cases, R³ is H. In some cases R³ is alkyl, and in more specific cases, is methyl, ethyl, propyl, or isopropyl. In some cases, R³ is alkoxy, and in more specific cases, is methoxyl, ethoxyl, propoxyl, or isopropoxyl, or even more specific cases, is methoxy or ethoxy.

Further disclosed herein are compositions comprising a compound as disclosed herein and a pharmaceutically acceptable carrier.

Also disclosed herein are methods comprising contacting a cell with a compound disclosed herein in an amount effective to decrease activity of IKKβ. In various cases, the contacting is in vitro. In other cases, the contacting is in vivo. In various cases, the IKKβ is a hyperphosphorylated form of IKKβ.

Further disclosed herein are methods of inhibiting NFκB or mTOR signaling pathway comprising contacting a cell with a compound as disclosed herein in an amount effective to inhibit the NFκB or mTOR signaling pathway.

Also disclosed herein are methods of treating a subject suffering from an IKKβ-dependent condition comprising administering to the subject a therapeutically effective amount of a compound as disclosed herein. In various cases, the condition is cancer, and in more specific cases, the cancer is pancreatic cancer, lymphoma, leukemia, colon cancer, colorectal cancer, familial adenomatous polyposis (FAP), hereditary non-polyposis cancer (HNPCC), colitis-associated cancer, gastric cancer, or breast cancer. In some cases, the condition is diabetes. In various cases, the condition is an inflammatory disease, and in more specific cases, is of rheumatoid arthritis, osteoarthritis, atherosclerosis, multiple sclerosis, chronic inflammatory demyelinating polyradiculoneuritis, asthma, inflammatory bowel disease, *helicobacter pylori*-associated gastritis, Crohn's disease, ulcerative colitis, or systemic inflammatory response syndrome. In some cases, the condition is a neurological disease, and in more specific cases, is of ischemic stroke, traumatic brain injury, seizure, and a neurodegenerative disorder, or even more specifically, Alzheimer's Disease, Parkinson's Disease, ALS, or Huntington's. In any one of the methods disclosed herein, the compound disclosed herein can be administered in addition to a second therapeutic.

Further disclosed herein are electroluminescent devices comprising a compound as disclosed herein. In some specific cases, the compound has a formula (IA) or (IB):

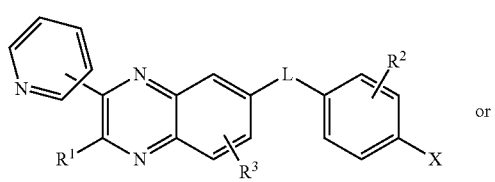

(IA)

or

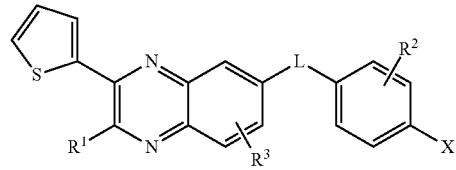

(IB)

wherein R¹ is 2-pyridyl, 3-pyridyl, 4-pyridyl, or thiophenyl. Also disclosed herein are organic electroluminescent devices which comprise a cathode, an anode, and an organic thin film layer comprising at least one layer sandwiched between the cathode and the anode, wherein the at least one layer comprises a compound as disclosed herein, wherein the compound has a blue fluorescence.

BRIEF DESCRIPTION OF THE FIGURES

FIG. 1. (D) The NF-κB pathway was activated by TNF-α (20 ng/mL) in cells treated with and without 13-197 (20 μM). Cell lysates were generated at indicated times and probed for p-IκBα, total-IκBα and tubulin.

FIG. 1. (E) Cell lysates were generated at the indicated times post TNF-α (20 ng/mL) stimulation with and without 13-197 (20 μM). The lysates were subjected to reciprocal IP-IB with NF-κB (p65) and IκBα antibodies.

FIG. 1. (F) An ELISA assay to probe the effect of 13-197 on the kinase activity of full length IKKβ (n=2).

FIG. 1. (G) Proposed model and potential target of 13-197.

FIG. 3. (F) MiaPaCa2 cells were treated with 11 μM of 13-197. After 24 h the cells were subjected to a live/dead assay (n=3). (G) Invasion of cells through matrigel coated microporous polycarbonate membrane was measured in the presence and absence of 13-197 (n=3). Transwell serum driven migration of cells in the presence and absence of 13-197 was measured after a 24 h incubation. (n=3). P<0.005 and *P<0.0005

DETAILED DESCRIPTION

Figures 1A, 1B, 1C, 1D, 1E, 1F:
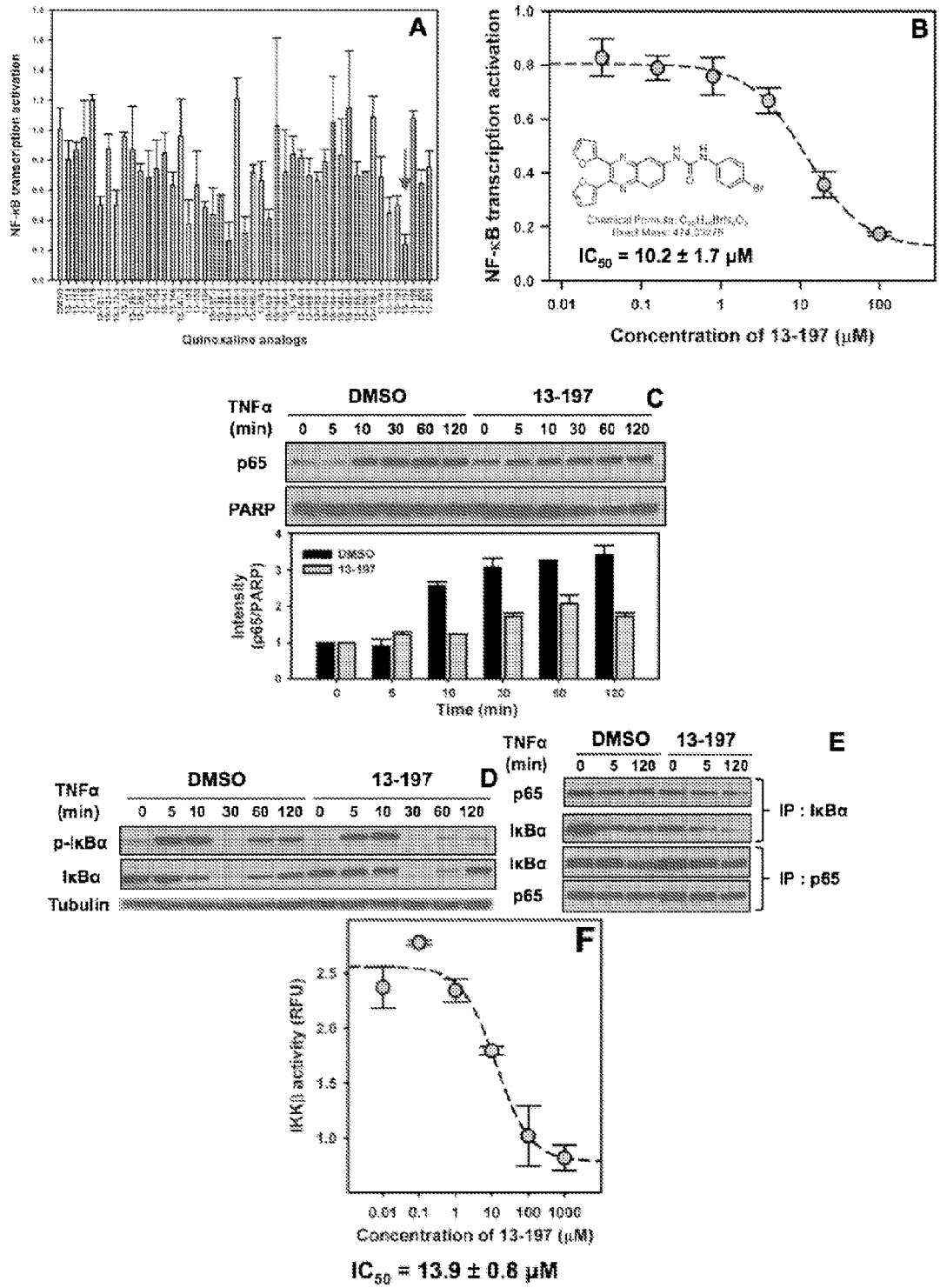
FIG. 1. (A) Subset of a focused library screened to identify inhibitors of TNF-α driven NF-κB activation. (B) Representative follow-up dose response curve with 13-197. (C) Representative blot showing the inhibition of TNF-α mediated NF-κB nuclear translocation by 13-197.

Disclosed herein are compounds having a structure of formula (I) and methods of inhibiting NF-κB, or more specifically inhibiting IKKβ, using a compound as disclosed herein.

The compounds disclosed herein have a structure of formula (I):

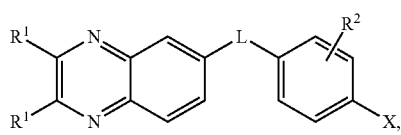

wherein each $R^1$ is independently heteroaryl, aryl, or alkyl; L is selected from —NHC(O)NH—, —NH—SO$_2$—, —NHC(O)CH$_2$—, —NHC(S)NH—,

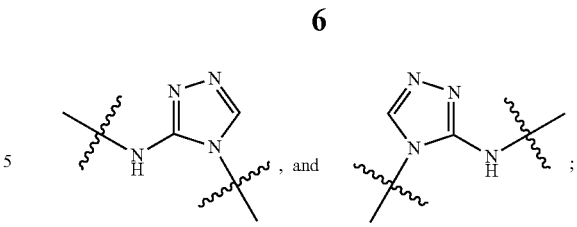

X is halo, alkyl, alkoxy, CO$_2$alkyl, COalkyl, or haloalkyl; $R^2$ is H, alkyl, alkoxy, CO$_2$alkyl, COalkyl, or haloalkyl; or a salt, hydrate, or solvate thereof.

In various embodiments disclosed herein, the compound of formula (I) has each $R^1$ the same. In some specific embodiments disclosed herein, at least one $R^1$ is furanyl or phenyl. In some specific embodiments disclosed herein, at least one $R^1$ is pyridyl or thiophenyl (also referred to as thienyl). In some specific embodiments disclosed herein, at least one $R^1$ is alkyl. In various embodiments disclosed herein, L is

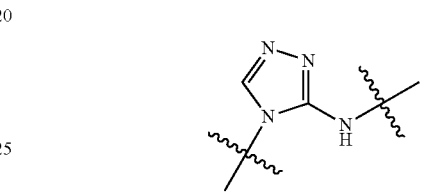

or —NHC(O)NH—. In various embodiments disclosed herein, X is Br. In some specific embodiments disclosed herein, X is Br, OMe, CO$_2$Me, CF$_3$, or COMe. In various embodiments disclosed herein, $R^2$ is H. In various embodiments disclosed herein, $R^2$ is CF$_3$, OMe, or Me.

As used herein, "alkyl" refers to monovalent alkyl groups having 1 to 20 carbon atoms. This term is exemplified by groups such as methyl, ethyl, propyl, isopropyl, butyl, sec-butyl, t-butyl, hexyl and the like. Linear and branched alkyls are included. The alkyl group can be a specific number of carbon atoms, as exemplified by the use of $C_x$-$C_y$, where x and y are integers. The compounds disclosed herein can have a $C_4$-$C_{20}$alkyl or more specifically a $C_4$-$C_{10}$alkyl substituent.

As used herein, the term "alkylene" refers to an alkyl group having a substituent. For example, the term "alkylenearyl" refers to an alkyl group substituted with an aryl group.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "alkoxy" used herein refers to an —Oalkyl group.

Asymmetric carbon atoms can be present. All such isomers, including diastereomers and enantiomers, as well as the mixtures thereof, are intended to be included in the scope of the disclosure herein. In certain cases, compounds can exist in tautomeric forms. All tautomeric forms are intended to be included in the scope of the disclosure herein. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated.

The salts, e.g., pharmaceutically acceptable salts, of the disclosed therapeutics may be prepared by reacting the appropriate base or acid with a stoichiometric equivalent of the therapeutic.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include anions, for example sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, and mandelate. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Similarly, pharmaceutically acceptable derivatives (e.g., esters), metabolites, hydrates, solvates and prodrugs of the therapeutic may be prepared by methods generally known to those skilled in the art. Thus, another embodiment provides compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the therapeutic. As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates. Examples of pharmaceutically-acceptable prodrug types are described in Higuchi and Stella, *Prodrugs as Novel Delivery Systems*, Vol. 14 of the A.C.S. Symposium Series, and in Roche, ed., *Bioreversible Carriers in Drug Design*, American Pharmaceutical Association and Pergamon Press, 1987, both of which are incorporated herein by reference.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to a disclosed therapeutic. The compounds and compositions described herein may also include hydrates and solvates. As used herein, the term "solvate" refers to a complex formed by a solute (herein, the therapeutic) and a solvent. Such solvents for the purpose of the embodiments preferably should not negatively interfere with the biological activity of the solute. Solvents may be, by way of example, water (e.g., forms a hydrate), ethanol, or acetic acid.

Some specific compounds disclosed herein include those shown in the below Scheme:

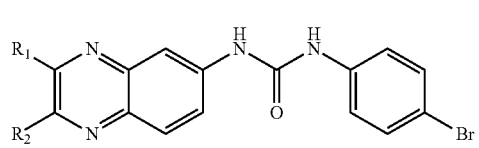

12A

-continued
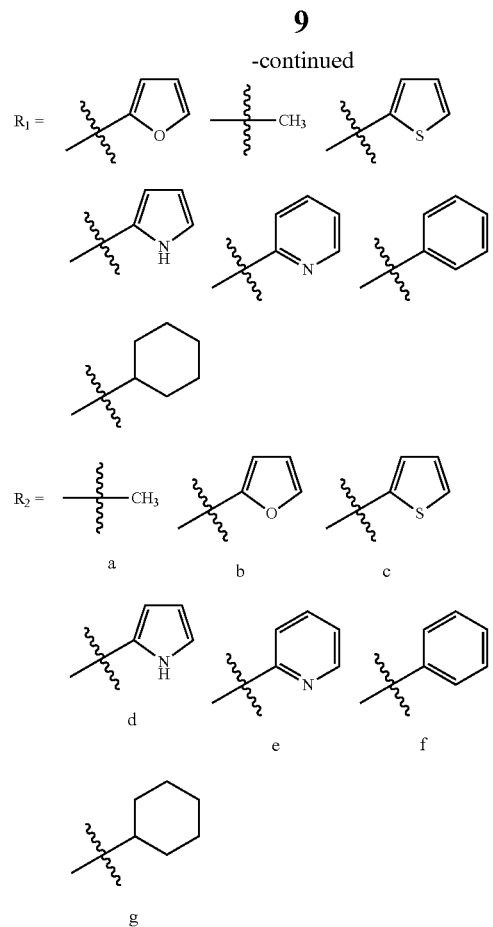
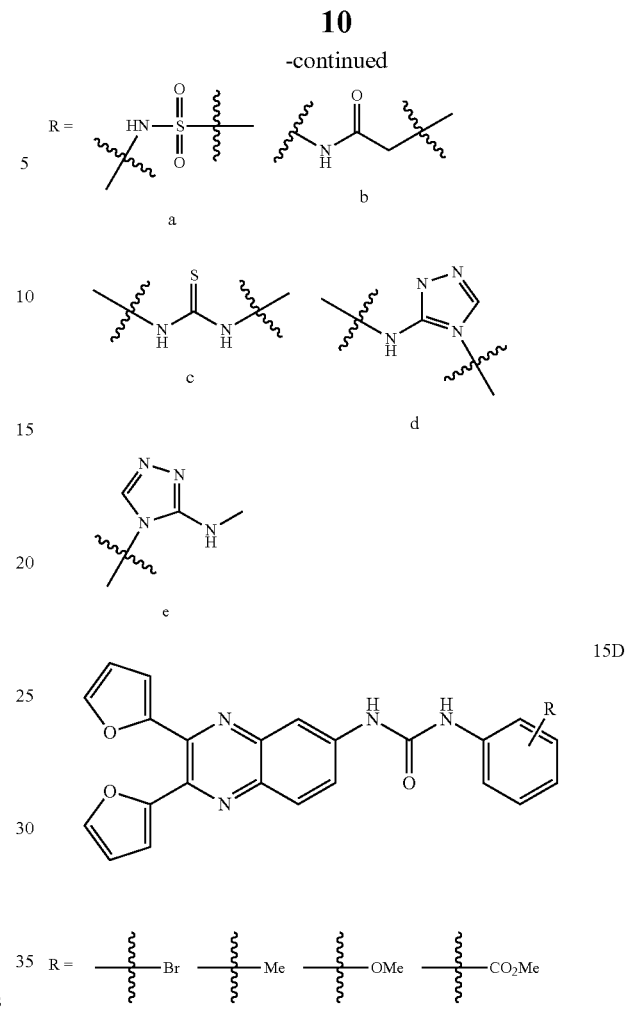
Specific compounds disclosed herein include
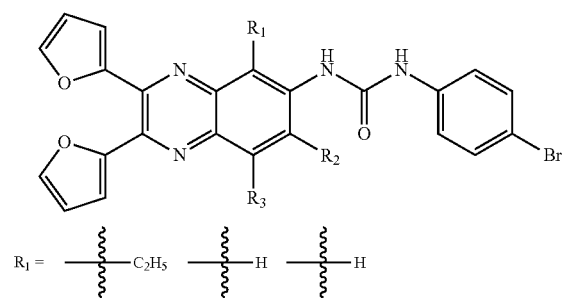
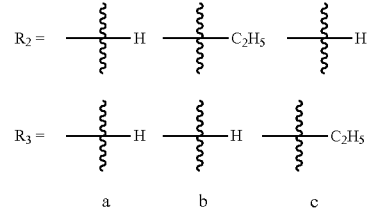
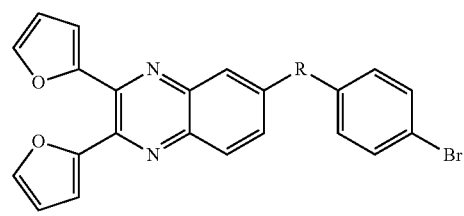
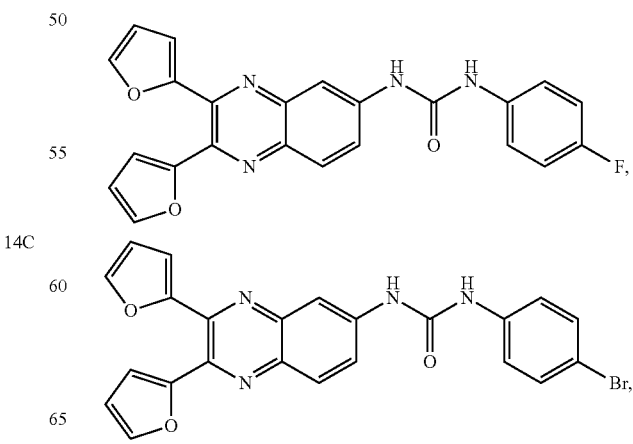

-continued
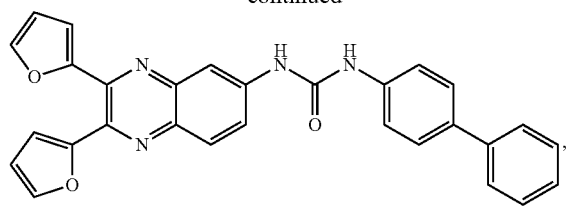
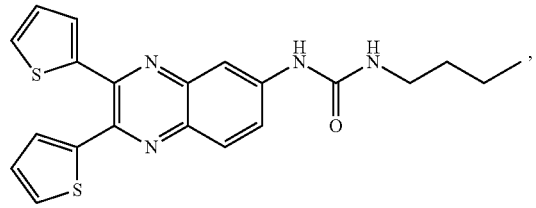
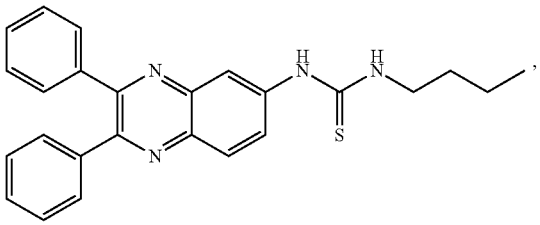
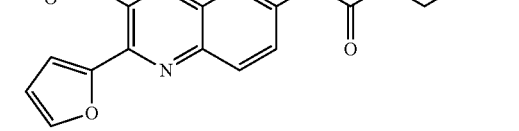
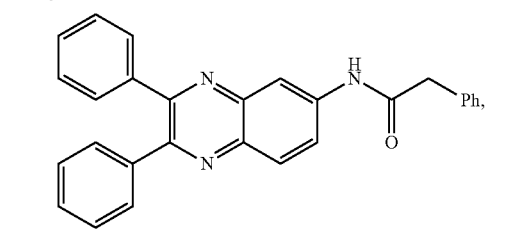
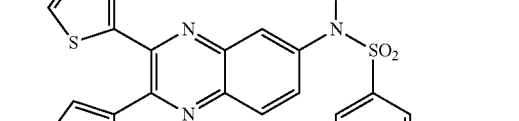
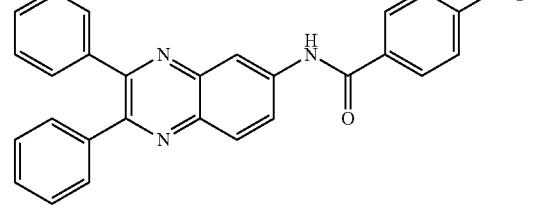
-continued
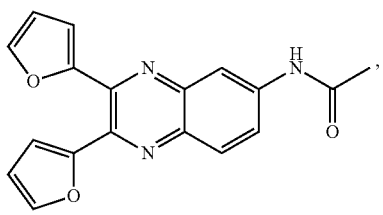
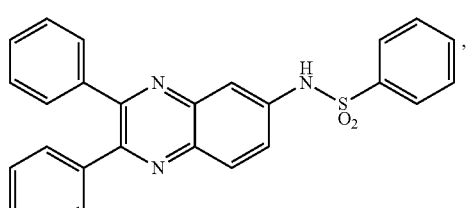
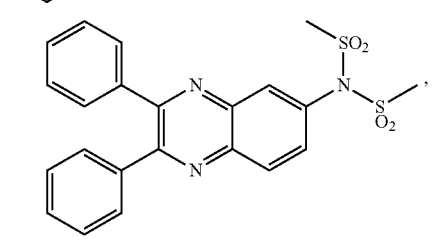
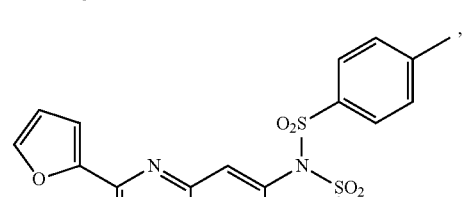
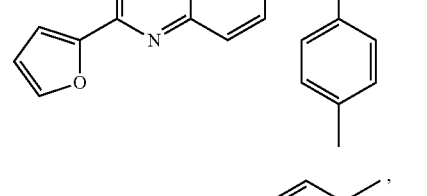
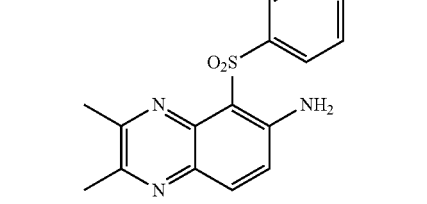
or a salt, hydrate or solvate thereof.
Other specific compounds contemplated include
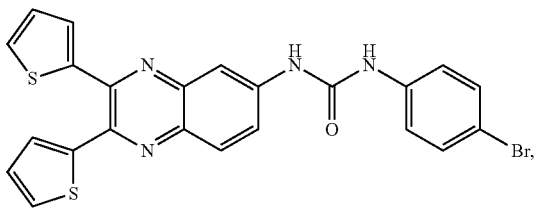

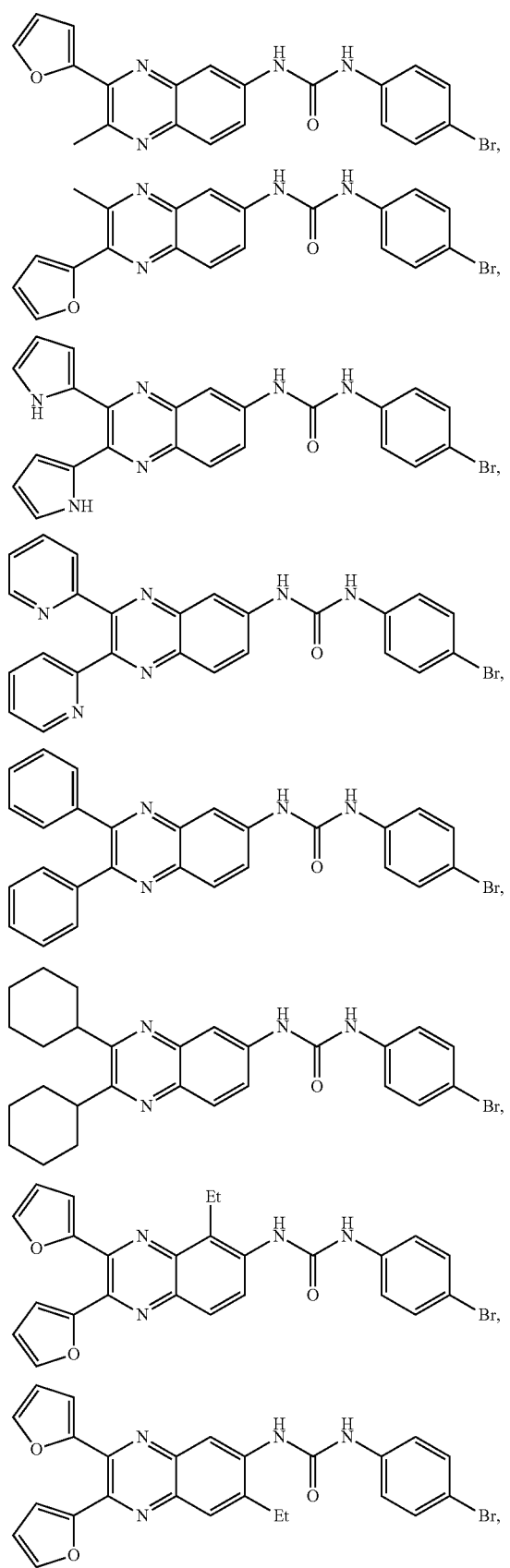
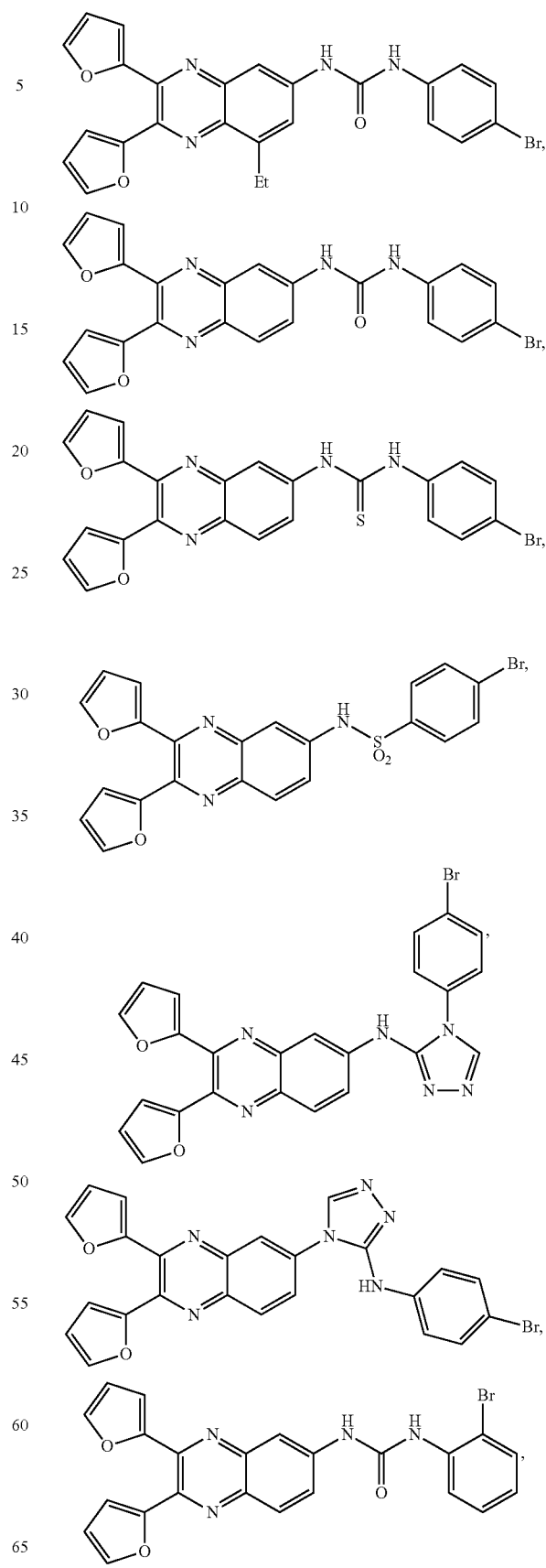

-continued or a salt, hydrate, or solvate thereof.

Still other specific compounds contemplated include

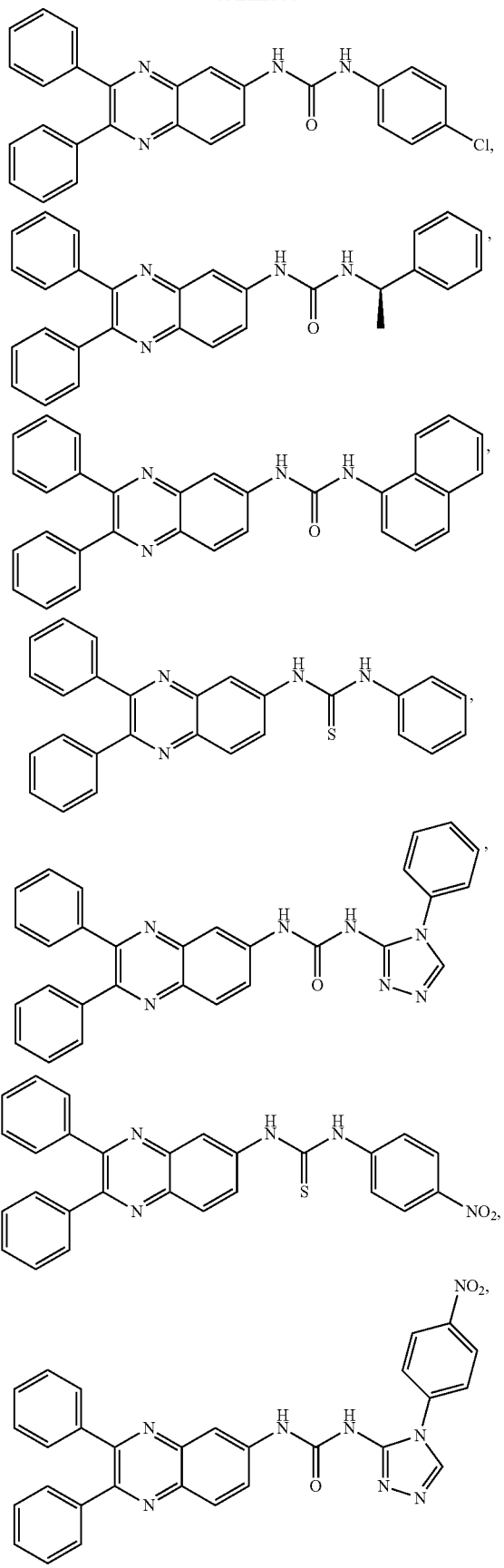

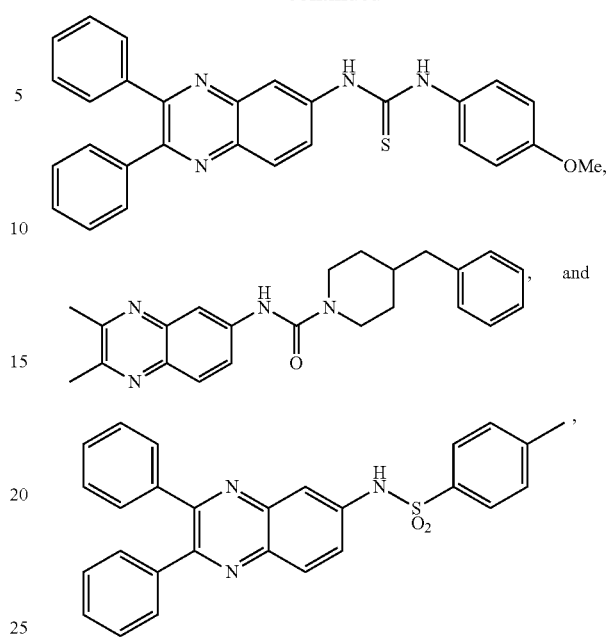

or a salt, hydrate or solvate thereof.

Yet other specific compounds are contemplated solely for use in the disclosed therapeutic methods and/or organic electroluminescent devices and methods described in detail below. These compounds are not contemplated as compounds per se and are therefore specifically excluded from the genus of compounds of formula (I) described above. These compounds include:

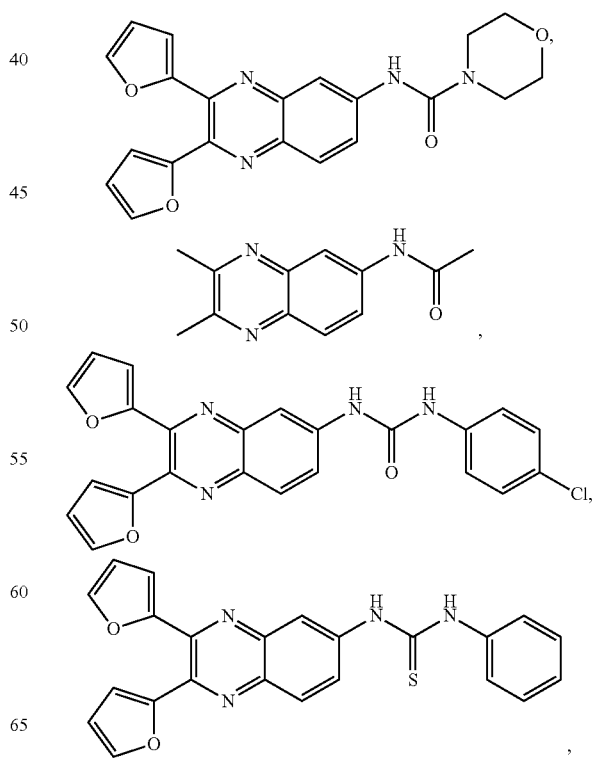

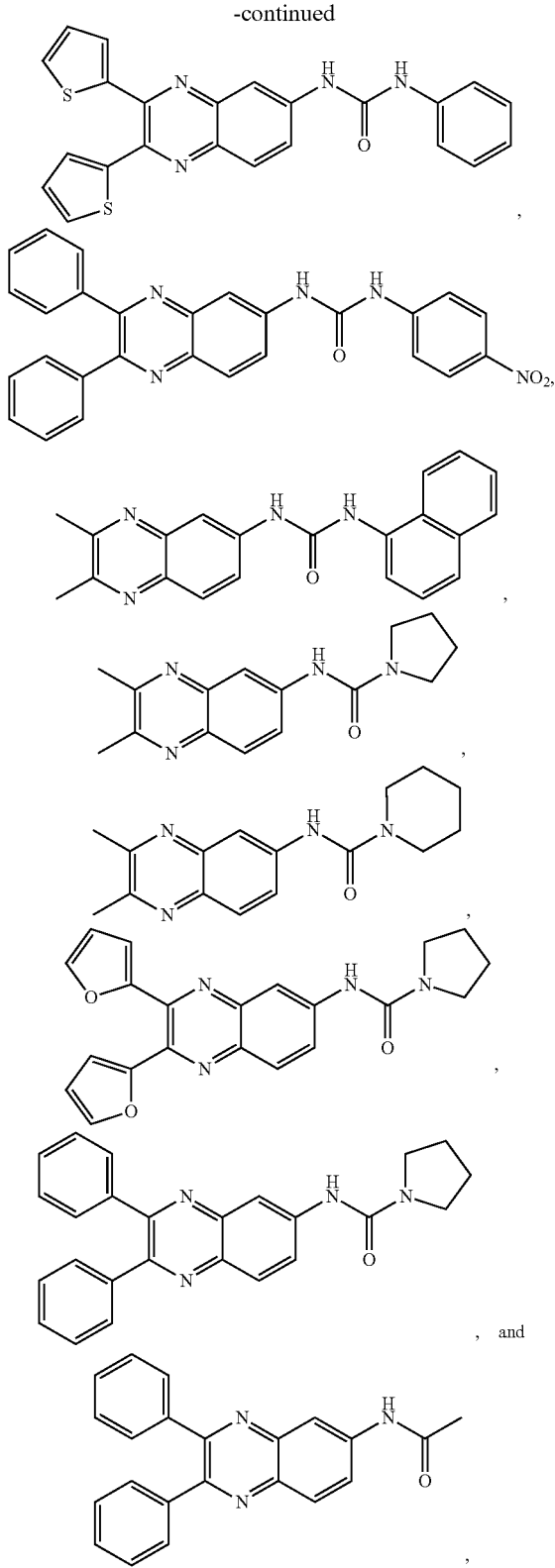

or a salt, hydrate, or solvate thereof.

Therapeutic Methods

The present invention provides IKKβ inhibitors, as exemplified by compounds of structural formula (I), for the treatment of a variety of diseases and conditions wherein inhibition of IKKβ has a beneficial effect. In some cases, the compounds disclosed herein inhibit the NF-κB pathway and/or the mTOR pathway. In one embodiment, the present invention relates to a method of treating an individual suffering from a disease or condition wherein inhibition of IKKβ, NF-κB pathway and/or the mTOR pathway provides a benefit comprising administering a therapeutically effective amount of a compound of structural formula (I) to an individual in need thereof.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The compounds of structural formula (I) therefore can be used to treat a variety of diseases and conditions where modulation (e.g., inhibition or activiation) of IKKβ, NF-κB pathway and/or the mTOR pathway provides a benefit. Examples of such diseases and condition include, but are not limited to cancer, diabetes, an inflammatory disease, and a neurological disease.

The disclosed methods are useful for treating cancer, for example, inhibiting cancer growth, including complete cancer remission, for inhibiting cancer metastasis, and for promoting cancer resistance. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

The term "cancer resistance" refers to an improved capacity of a subject to resist cancer growth, in particular growth of a cancer already had. In other words, the term "cancer resistance" refers to a decreased propensity for cancer growth in a subject.

In one aspect, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellulare, glandular, granulose cell, hepatocellular, Wirthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may be targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, acute lymphocytic, acute myelogenous leukemia, chronic myelogenous, hairy cell, erythroleukemia, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocytic, monocytic, prolymphocytic, promyelocytic, micromyeloblastic, megakaryoblastic, megakaryoctyic, rieder cell, bovine, aleukemic, mast cell, myelocytic, plasma cell, subleukemic, multiple myeloma, nonlymphocytic, chronic myelogenous leukemia, chronic lymphocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestimal cancers that may be targeted include extrahepatic bile duct cancer, colon cancer, colon and rectum cancer, colorectal cancer, gallbladder cancer, gastric (stomach) cancer, gastrointestinal carcinoid tumor, gastrointestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer à deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenström's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

Specific cancers contemplated include acute lymphoblastic leukemia (ALL); acute myeloid leukemia (AML), adrenocortical carcinoma, AIDS-related cancer, Kaposi sarcoma, lymphoma, anal cancer, appendix cancer, astrocytomas, atypical teratoid/rhabdoid tumor, basal cell carcinoma, bile duct cancer, bladder cancer, bone cancer, osteosarcoma, malignant fibrous histiocytoma, brain stem glioma, brain tumor, astrocytoma, brain and spinal cord tumor, brain stem glioma, CNS atypical teratoid/rhabdoid tumor, CNS embryonal tumor, craniopharyngioma, ependymoblastoma, ependymoma, medulloblastoma, medulloepithelioma, pineal parenchymal tumor, supratentorial primitive neuroectodermal tumor, pineoblastoma, breast cancer, bronchial tumor, Burkitt lymphoma, non-Hodgkin lymphoma, carcinoid tumor, cervical cancer, chordoma, chronic lymphocytic leukemia (CLL), chronic myelogenous leukemia (CML), chronic myeloproliferative disorder, colon cancer, colorectal cancer, craniopharyngioma, cutaneous T-cell lymphoma, embryonal tumor, endometrial cancer, ependymoblastoma, ependymoma, esophageal cancer, esthesioneuroblastoma, Ewing sarcoma, extracranial germ cell tumor, extragonadal germ cell tumor, eye cancer, intraocular melanoma, retinoblastoma, gallbladder cancer, gastric (stomach) cancer, gastrointestinal carcinoid tumor, gastrointestinal stromal tumor (GIST), gestational trophoblastic tumor, glioma, hairy cell leukemia, head and neck cancer, heart cancer, hepatocellular (liver) cancer, histiocytosis, langerhans cell, Hodgkin lymphoma, hypopharyngeal cancer, intraocular melanoma, islet cell tumor, renal cell cancer, langerhans cell histiocytosis, laryngeal cancer, leukemia, lip and oral cavity cancer, liver cancer, lobular carcinoma in situ (LCIS), lung cancer, lymphoma, macroglobulinemia, medulloblastoma, medulloepithelioma, melanoma, Merkel cell carcinoma, mesothelioma, metastatic squamous neck cancer, mouth cancer, multiple endocrine neoplasia syndrome, multiple myeloma/plasma cell neoplasm, mycosis fungoide, myelodysplastic syndrome, myelodysplastic/myeloproliferative neoplasm, nasal cavity and paranasal sinus cancer, nasopharyngeal cancer, neuroblastoma, non-small cell lung cancer, oral cancer, oropharyngeal cancer, ovarian cancer, pancreatic cancer, papillomatosis, paraganglioma, parathyroid cancer, penile cancer, pharyngeal cancer, pheochromocytoma, pineal parenchymal tumor, pituitary tumor, plasma cell neoplasm, pleuropulomary blastoma, prostate cancer, rectal cancer, renal pelvis and ureter transitional cell cancer, retinoblastoma, rhabdomyosarcoma, salivary gland cancer, sarcoma, uterine sarcoma, soft tissue sarcoma, skin cancer, small cell lung cancer, small intestines cancer, squamous cell carcinoma, stomach cancer, T-cell lymphoma, testicular cancer, throat cancer, thymoma, thymic cancer, thyroid cancer, gestational trophoblastic cancer, vaginal cancer, vulvar cancer, Wilms tumor, and Waldenstrom macroglobulinemia. Specific cancers contemplated include pancreatic cancer, lymphoma, leukemia, colon cancer, colorectal cancer, familial adenomatous polyposis (FAP), hereditary non-polyposis cancer (HNPCC), colitis-associated cancer, gastric cancer, and breast cancer. Specific inflammatory diseases contemplated include arthritis, rheumatoid arthritis, osteoarthritis, atherosclerosis, multiple sclerosis, chronic inflammatory demyelinating polyradiculoneuritis, asthma, inflammatory bowel disease, *helicobacter* pylori-associated gastritis, Crohn's disease, ulcerative colitis, and systemic inflammatory response syndrome.

The disclosed methods are useful for treating neurological disorders. For example, the NF-κB pathway is involved in various central nervous system (CNS) diseases such as ischemic stroke, traumatic brain injury, seizures, and neurodegenerative disorders. Non-limiting examples of neurodegenerative disorders include Alzheimer's Disease, Parkinson's Disease, ALS, and Huntington's. The role of the NF-κB pathway in CNS disease is described in greater detail in Mattson et al., *J. Clinical Invest.*, 107(3):247 (2001).

A method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of IKKβ provides a benefit, packaged separately or together, and an insert having instructions for using these active agents.

The methods disclosed herein also include the use of a compound or compounds as described herein together with one or more additional therapeutic agents for the treatment of a disease. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some cases, a compound disclosed herein is administered and/or formulated with a second therapeutic, for example, a chemotherapeutic (e.g., an anti-cancer agent).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors, and nanoparticles.

Synthesis of Compounds

The compounds disclosed herein can be synthesized through any means available to the synthetic chemist and in view of the guidance of the schemes below. Non-limiting examples for preparing compounds disclosed herein is provided below.

Scheme 1

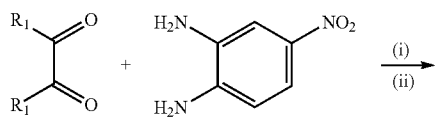

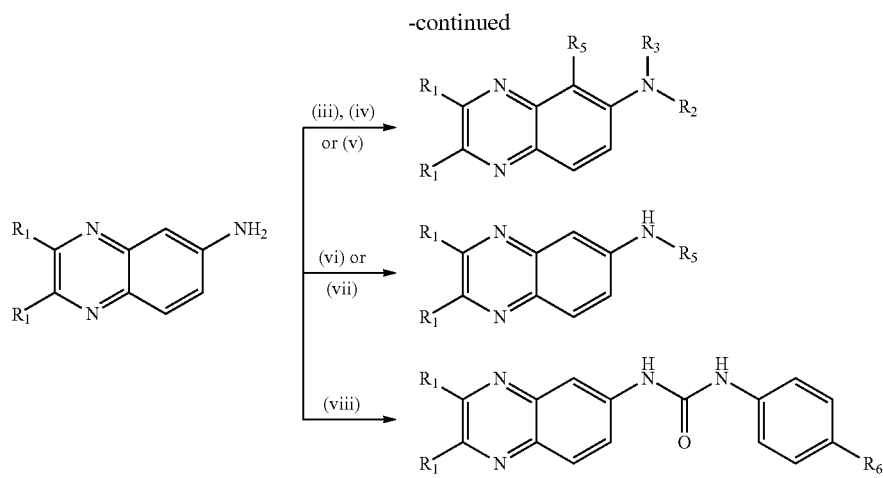

Exemplary reagents and conditions for reactions of Scheme 1 are: (i) Ethanol, reflux, 36-48 h; (ii) Pd/C, H$_2$, ethanol, room temperature, 6-8 h; (iii) R$_2$NCO, DIPEA, DCM 24-72 h; (iv) R$_2$COCl, DCM, 4 h; (v) TsCl, TEA, DCM 6 h; (vi) R$_5$NCS (2 eq), DCM, reflux; (vii) Triphosgene, DIPEA, DCM, 4 h; Amine, DCM, 8-24 h; (viii) R$_6$PhNCO (1.5 eq), DIPEA, DCM, 12-24 h.

Exemplary compounds prepared by the synthetic scheme outlined in Scheme 1 are listed in Table 1.

TABLE 1

| Entry | R$_1$ | R$_2$ | R$_3$ | R$_4$ |
|---|---|---|---|---|
| 5a | Methyl | —COCH$_3$ | —H | —H |
| 5b | Furanyl | —COCH$_3$ | —H | —H |
| 5c | Thienyl | —COCH$_3$ | —H | —H |
| 5d | Phenyl | —COCH$_3$ | —H | —H |
| 5e | Methyl | —CONHPh | —H | —H |
| 5f | Furanyl | —CONHPh | —H | —H |
| 5g | Thienyl | —CONHPh | —H | —H |
| 5h | Phenyl | —CONHPh | —H | —H |
| 5i | Methyl | —H | —H | —SO$_2$Tol |
| 5j | Furanyl | —SO$_2$Tol | —SO$_2$Tol | —H |
| 5k | Thienyl | —SO$_2$Tol | —SO$_2$Tol | —H |
| 5l | Phenyl | —SO$_2$Tol | —H | —H |

| | R$_1$ | R$_5$ | | |
|---|---|---|---|---|
| 6a | Furanyl | —CS-Phenyl | | |
| 6b | Thienyl | —CS-Phenyl | | |
| 6c | Phenyl | —CS-Phenyl | | |
| 6d | Furanyl | —CS-(4-Nitro)-Phenyl | | |
| 6e | Thienyl | —CS-(4-Nitro)-Phenyl | | |
| 6f | Phenyl | —CS-(4-Nitro)-Phenyl | | |

TABLE 1-continued

| 6g | Methyl | —CO-Pyrrolidine |
| 6h | Furanyl | —CO-Pyrrolidine |
| 6i | Phenyl | —CO-Pyrrolidine |
| 6j | Methyl | —CO-(4-Benzyl)-Piperidine |
| 6k | Furanyl | —CO-(4-Benzyl)-Piperidine |
| 6l | Methyl | —CO-Piperdine |
| 6m | Furanyl | —CO-Morpholine |

| | R$_1$ | R$_6$ |
|---|---|---|
| 7a | Furanyl | —F |
| 7b | Furanyl | —Cl |
| 7c | Furanyl | —Br |
| 7d | Furanyl | -Phenyl |

The compounds were screened in a growth inhibition assay at 20 μM over a 72 h period in a panel of cancer cell lines (lung-A549; pancreatic-Aspc1; colon-HT29; breast-MDAMB231; prostate-PC3; ovarian-SKOV3 and bone-U2OS) and the results are summarized in Table 2. In the 5 compound series only 5a, 5b and 5f inhibited growth of the various cancer cell lines. This suggests that the furan substitutions at the 2,3-positions are clearly better than the other three. It also suggests that sulfonamide substitution at the 6-position is not suitable for the growth inhibitory activity. The screening results in the 6 compound series again show that all the furan compounds (6a, 6d, 6 h, 6k and 6m) were active. It also shows that substitution at the 4-position of the phenyl thioureas plays a role in the biological activity (6b and 6c vs. 6e and 6f). This size effect was also observed with the urea compounds from the secondary amine (6j vs. 6l and 6k vs. 6m).

TABLE 2

| | % Growth inhibition at 20 μM | | | | | | |
|---|---|---|---|---|---|---|---|
| Entry | A549 | AsPC1 | HT29 | MDA-MB-231 | PC3 | SKOV3 | U2OS |
| 5a | 23.4 ± 3.3 | 26.2 ± 2.8 | 31.7 ± 2.8 | 25.7 ± 5.1 | 21.8 ± 15.1 | 4.0 ± 3.6 | 31.4 ± 3.6 |
| 5b | 57.8 ± 7.0 | Inactive | 7.6 ± 5.1 | 20.3 ± 5.9 | 57.7 ± 9.4 | 9.0 ± 3.4 | Inactive |
| 5c | Inactive | Inactive | Inactive | Inactive | Inactive | Inactive | Inactive |
| 5d | Inactive | Inactive | Inactive | Inactive | Inactive | Inactive | Inactive |
| 5e | Inactive | Inactive | Inactive | Inactive | Inactive | Inactive | Inactive |
| 5f | 54.6 ± 2.6 | 9.6 ± 6.6 | 52.1 ± 11.6 | 31.3 ± 10.7 | 70.6 ± 1.3 | 24.7± 1.1 | 59.6 ± 1.6 |
| 5g | Inactive | Inactive | Inactive | Inactive | Inactive | Inactive | Inactive |
| 5h | Inactive | Inactive | Inactive | Inactive | Inactive | Inactive | Inactive |
| 5i | Inactive | Inactive | Inactive | Inactive | Inactive | Inactive | Inactive |
| 5j | Inactive | Inactive | Inactive | Inactive | Inactive | Inactive | Inactive |
| 5k | Inactive | Inactive | Inactive | Inactive | Inactive | Inactive | Inactive |

TABLE 2-continued

| | % Growth inhibition at 20 µM | | | | | | |
|---|---|---|---|---|---|---|---|
| Entry | A549 | AsPC1 | HT29 | MDA-MB-231 | PC3 | SKOV3 | U2OS |
| 5l | Inactive | Inactive | Inactive | Inactive | Inactive | Inactive | Inactive |
| 6a | 18.0 ± 0.1 | Inactive | 26.1 ± 15.0 | 19.1 ± 12.5 | 56.8 ± 1.4 | Inactive | 21.4 ± 8.4 |
| 6b | Inactive | Inactive | Inactive | Inactive | Inactive | Inactive | Inactive |
| 6c | Inactive | Inactive | Inactive | Inactive | Inactive | Inactive | Inactive |
| 6d | 19.2 ± 8.9 | Inactive | 42.0 ± 1.9 | 9.0 ± 4.7 | 43.4 ± 9.3 | Inactive | 32.2 ± 0.1 |
| 6e | Inactive | Inactive | 23.9 ± 27.8 | 53.3 ± 7.2 | 19.5 ± 37.4 | Inactive | 50.6 ± 3.9 |
| 6f | 16.6 ± 11.2 | 55.5 ± 25.4 | 81.2 ± 0.7 | 72.6 ± 0.7 | 81.0 ± 8.5 | 55.8 ± 30.7 | 76.1 ± 0.4 |
| 6g | Inactive | Inactive | Inactive | Inactive | Inactive | Inactive | Inactive |
| 6h | 23.3 ± 2.9 | 11.6 ± 4.2 | 16.7 ± 3.7 | 18.2 ± 7.0 | 53.1 ± 9.9 | 16.9 ± 4.9 | 46.5 ± 4.4 |
| 6i | 11.0 ± 1.3 | 29.4 ± 9.8 | Inactive | 16.7 ± 3.9 | 56.9 ± 2.7 | 18.5 ± 4.3 | 54.2 ± 2.2 |
| 6j | 40.3 ± 1.9 | Inactive | 16.3 ± 10.1 | 12.4 ± 5.0 | 30.6 ± 11.6 | 8.9 ± 5.1 | 33.5 ± 0.4 |
| 6k | 93.1 ± 7.8 | >100 | 55.2 ± 4.1 | 90.8 ± 4.5 | >100 | 47.6 ± 2.5 | 80.3 ± 2.4 |
| 6l | Inactive | Inactive | Inactive | Inactive | Inactive | Inactive | Inactive |
| 6m | 39.7 ± 12.8 | Inactive | 19.4 ± 3.6 | 10.9 ± 5.0 | 48.9 ± 7.5 | Inactive | Inactive |
| 7a | >100 | >100 | 74.2 ± 5.2 | 38.4 ± 2.7 | 90.7 ± 4.1 | Inactive | 55.6 ± 6.6 |
| 7b | 99.2 ± 5.2 | 81.1 ± 2.0 | 86.3 ± 7.7 | 92.5 ± 6.6 | 86.4 ± 1.1 | 55.8 ± 24.1 | 87.4 ± 1.1 |
| 7c | >100 | >100 | 88.6 ± 4.6 | >100 | >100 | 94.9 ± 7.9 | >100 |
| 7d | 13.8 ± 9.8 | Inactive | 72.4 ± 7.6 | 50.2 ± 8.9 | 88.5 ± 1.9 | Inactive | 46.9 ± 7.4 |

These results prompted us to synthesize, four additional compounds to probe the size effect at the 4-position on a phenyl urea (7a-d). Evaluation of these analogs in the growth inhibition assay clearly showed a size effect and compound 7c with bromo substituion at the 4-position was identified as the best compound. A dose-response study with compound 7c shows low-µM $GI_{50}$ values against a panel of cancer cell lines (Table 3). In summary this iterative synthesis and screening effort show that the furan substitution at the 2,3-position, a urea at the 6-position and the substituent at the para-position of a phenyl urea are important for the biological activity. These studies also resulted in the identification 7c with low-µM $GI_{50}$ values against a panel of cancer cell lines.

TABLE 3

| Cell line | $GI_{50}$ (µM) |
|---|---|
| A549 | 6.4 ± 3.0 |
| AsPC1 | 17.3 ± 0.9 |
| HT29 | 12.1 ± 7.4 |
| MDA-MB-231 | 8.4 ± 0.9 |
| PC3 | 5.9 ± 2.7 |
| SKOV3 | 16.8 ± 5.2 |
| U2OS | 10.8 ± 0.2 |

Figure 5:
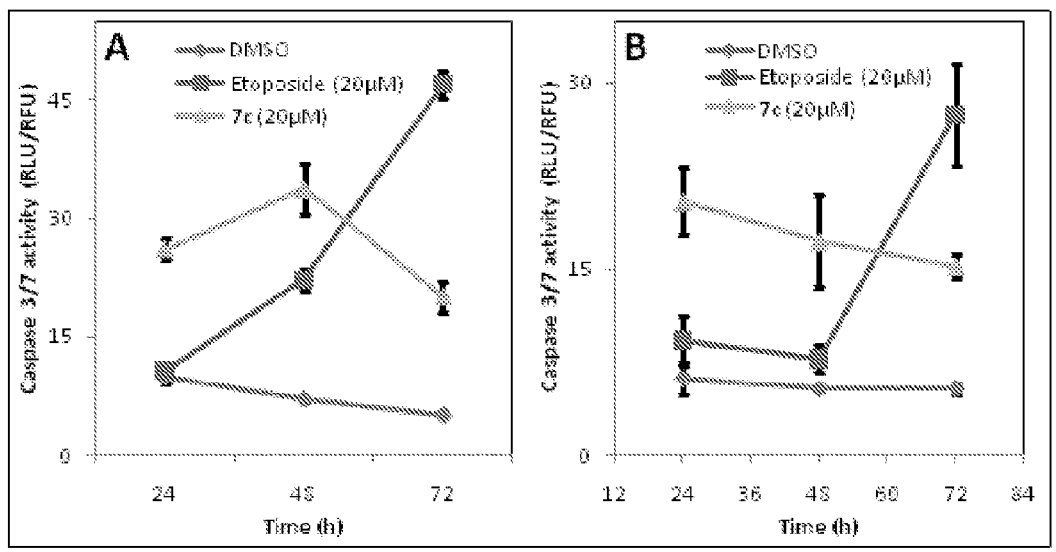
FIG. 5 shows induction of caspase 3/7 activity by 7c (also referred to throughout this disclosure as 13-197) and etoposide a known chemotherapeutic agent in MDA-MB-231 breast cancer cells (A) and PC3 prostate cancer cells (B).

Caspases are a class of cysteine proteinases that are activated during apoptosis and measuring caspase activity is often used to detect activation of apoptotic signaling. To determine if the growth inhibitory effects observed with 7c in various cancer cell lines were a result of programmed cell death, the ability of 7c to induce caspase-3/7 was explored. The results show that 7c induces caspase 3/7 much more rapidly compared to the positive control (Etoposide) in MDA-MB-231 and PC3 cells (FIGS. 5 A and B) and the induction is sustained for 72 h in these cell lines.

Figure 6:
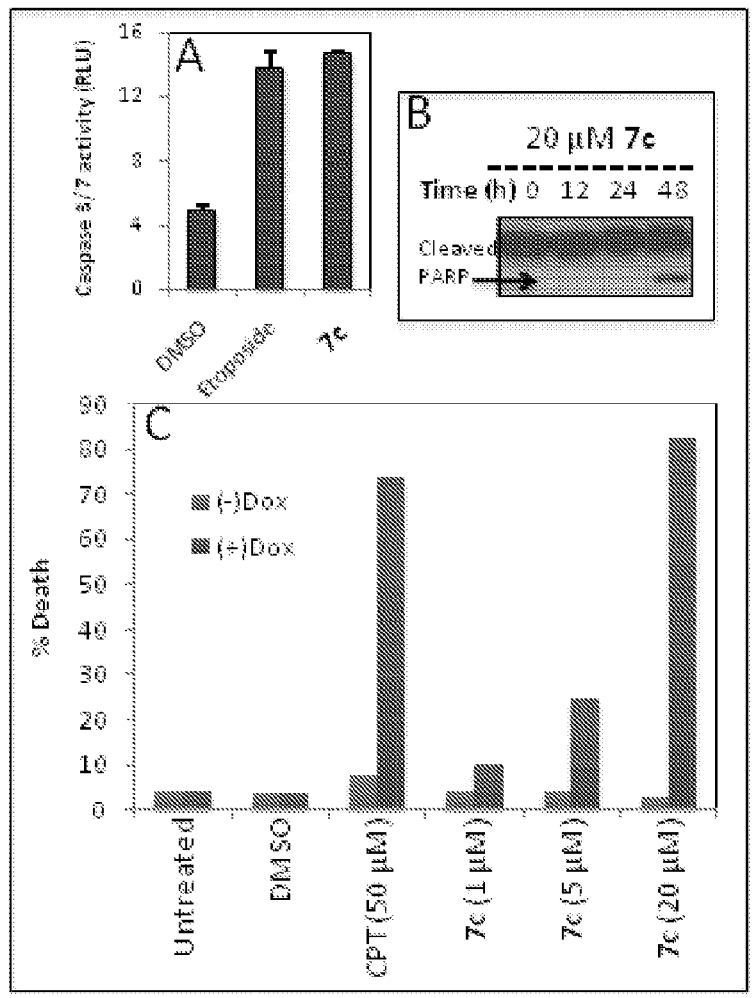
FIG. 6 shows apoptosis studies in Hela cells: (A) Induction of caspase 3/7 by 7c and etoposide. (B) PARP cleavage induced by 7c assessed by Western blot analyses. (C) Mcl-1 dependent induction of apoptosis by 7c.

Bcl-xL, Bcl-2 and Mcl-1 are antiapoptotic proteins that are implicated in the survival of cancer cells. Bad3SA is the endogenous inhibitor of Bcl-xL and Bcl-2 but not Mcl-1. Using Hela cells that over express Bad3SA, we explored the mechanistic basis for the induction of apoptosis by 7c. In these cell lines expression of Bad3SA is under the control of Doxcycline (Dox). The apoptosis studies carried out in these cell lines are summarized in FIG. 6. As with the other cancer cell lines we observe induction of caspase 3/7 and PARP cleavage by 7c (FIGS. 6A and 6B respectively). We next carried out a dose response study with 7c in cells treated with Dox (1 µg/mL for 3 h) to induce Bad3SA [(+) Dox] and untreated cells [(−) Dox]. The cells were incubated with 7c and a positive control (DNA damaging agent Camptothecin, CPT) for 12 h. Cell death was measured by counting the number of condensed nuclei. A dose dependent increase in the induction of apoptosis in the (+) Dox cells was observed, indicating that 7c induces apoptosis in a Mcl-1 dependent manner (FIG. 6C).

In summary, a focused library of 2,3-substituted quinoxalin-6-amine analogs was synthesized and evaluated in a panel of cancer cell lines for growth inhibition. The preliminary structure activity relationship (SAR) showed bis-furan substitution at the 2,3-positions was favored. A comparison of a series of linkers between the 2,3-disubstituted quinoxaline and a substituted phenyl ring showed that a urea linker was optimal for the antiproliferative activity. In addition, the size of the substituent at the 4-position of the phenyl ring was important for the activity. These led to the identification of bisfuranylquinoxalineurea analog (7c) with low micromolar potency against the panel of cancer cell lines. The analog 7c induces caspase 3/7 activation, PARP cleavage and Mcl-1 dependent apoptosis.

Dosing and Pharmaceutical Formulations

The term "therapeutically effective amount," as used herein, refers to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein or known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

A compound of structural formula (I) used in a method of the present invention can be administered in an amount of about 0.005 to about 750 milligrams per dose, about 0.05 to about 500 milligrams per dose, or about 0.5 to about 250 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, 500, 550, 600, 650, 700, or 750 milligrams, including all doses between 0.005 and 750 milligrams.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of a disorder as disclosed herein (e.g., an anticancer agent or an anti-inflammatory agent).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Organic Electroluminescence

Compounds disclosed herein can be blue fluorescent. In particular, compounds wherein at least one $R^1$ is pyridyl (e.g., 2-, 3-, or 4-pyridyl) or thiophenyl exhibit a blue fluorescent property. More specifically, compounds having a structure of formula (IA) or (IB) can be blue fluorescent:

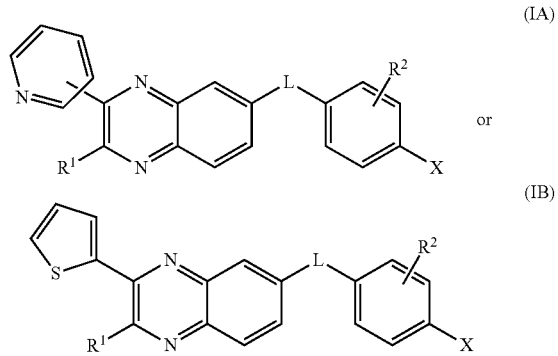

wherein $R^1$ is 2-pyridyl, 3-pyridyl, 4-pyridyl, or thiophenyl, and $R^2$, L, and X are as defined above.

Thus, compounds disclosed herein can be used as organic electroluminescent (EL) materials and devices. The light emission of the organic EL device is a phenomenon in which, when an electric field is applied across the two electrodes, electrons are injected from the cathode side and holes are injected from the anode side, the electrons recombine with the holes in the light emitting layer to induce an excited state, and then, when the excited state returns to the original state, it emits energy as light.

The organic EL device disclosed herein comprises an anode, a cathode and an organic thin film layer comprising at least one layer sandwiched between the anode and the cathode, wherein at least one layer in the organic thin film layer comprises a compound having a structure of formula (I).

The organic EL device disclosed herein emits bluish light, due to an energy gap. The material for organic EL devices can be a host material of the organic EL device. The host material is a material into which holes and electrons can be injected and which has the function of transporting holes and electrons and emitting fluorescent light by recombination of holes and electrons.

In the light emitting layer of the organic EL device, in general, the singlet exciton and the triplet exciton are contained in the formed excited molecules as a mixture, and it is reported that the triplet exciton is formed in a greater amount such that the ratio of the amount of the singlet exciton to the amount of the triplet exciton is 1:3. In conventional organic EL devices using the phosphorescence, the exciton contributing to the light emission is the singlet exciton, and the triplet exciton does not emit light. Therefore, the triplet exciton is ultimately consumed as heat, and the light is emitted by the singlet exciton which is formed in a smaller amount. Therefore, in these organic EL devices, the energy transferred to the triplet exciton causes a great loss in the energy generated by the recombination of holes and electrons.

In some embodiments, by using the material as disclosed herein for the phosphorescence device, the efficiency of light emission three times as great as that of a device using fluorescence can be obtained since the triplet exciton can be used for the emission of light. Further, in various embodiments, when the compound as disclosed herein is used for the light emitting layer of the phosphorescence device, an excited triplet level in an energy state higher than the excited triplet level of a phosphorescent organometallic complex comprising a metal selected from the Group 7 to 11 of the Periodic Table contained in the layer, is achieved; the film having a more stable form is provided; the glass transition temperature is higher (Tg: 80 to 160° C.); holes and/or electrons are efficiently transported; the compound is electrochemically and chemically stable; and the formation of impurities which may work as a trap or cause loss in the light emission is suppressed during the preparation and the use.

The organic EL device disclosed herein comprises a cathode, an anode and an organic thin film layer comprising at least one layer and sandwiched between the cathode and the anode. When the organic thin film layer comprises a single layer, a light emitting layer is formed between the anode and the cathode. The light emitting layer contains a light emitting material and may further contain a hole injecting material for transporting holes injected from the anode to the light emitting material or an electron injecting material for transporting electrons injected from the cathode to the light emitting material. In some cases, the light emitting material exhibits a high quantum efficiency of fluorescence, is able to transport both holes and electrons and/or forms a uniform thin layer. Examples of the organic EL device of the multi-layer type include organic EL devices comprising a laminate having a multi-layer construction such as (the anode/the hole injecting layer/the light emitting layer/the cathode), (the anode/the light emitting layer/the electron injecting layer/the cathode) and (the anode/the hole injecting layer/the light emitting layer/the electron injecting layer/the cathode).

For the light emitting layer, in addition to the compounds disclosed herein, conventional host materials, light emitting materials, doping materials, hole injecting materials and electron injecting materials and combinations of these materials can be used in combination. By using a multi-layer structure for the organic EL device, decreases in the luminance and the life due to quenching can be prevented, and the luminance of emitted light and the efficiency of light emission can be improved with other doping materials. By using other doping materials contributing to the light emission of the phosphorescence in combination, the luminance of emitted light and the efficiency of light emission can be improved in comparison with those of conventional devices.

In the organic EL device disclosed herein, the hole injecting layer, the light emitting layer and the electron injecting layer may each have a multi-layer structure. When the hole injecting layer has a multi-layer structure, the layer into which holes are injected from the electrode is called as a hole injecting layer, and the layer which receives holes from the hole injecting layer and transports holes to the light emitting layer is called as a hole transporting layer. Similarly, when the electron injecting layer has a multi-layer structure, the layer into which electron are injected from the electrode is called as an electron injecting layer, and the layer which receives electrons from the electron injecting layer and transports electrons to the light emitting layer is called as an electron transporting layer. The layers are selected in accordance with the energy levels of the material, heat resistance and adhesion with the organic thin film layers or the metal electrodes.

In the organic EL device disclosed herein, the electron transporting layer and the hole transporting layer can contain the material for organic EL devices of the present invention which comprises the compound represented by general formula (I).

Examples of the light emitting material and the host material which can be used for the organic thin film layer in combination with the compound represented by general formula (I) include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenyl-butadiene, coumarine, oxadiazole, aldazine, bis-benzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminoanthracene, diaminocarbazole, pyrane, thiopyrane, polymethine, melocyanine, oxinoid compounds chelated with imidazole, quinacridone, rubrene, stilbene-based derivatives and fluorescent pigments. However, the light emitting material and the host material are not limited to the compounds described above.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Preparation of Compounds of Table 1

Experimental Methods:

Unless otherwise specified, all reagents were purchased from commercial sources and were used without further purification. Flash chromatography was carried out on silica gel (200-400 mesh). $^1$H-NMR (300 MHz or 500 MHz) and $^{13}$C-NMR (75 MHz or 125 MHz) spectra were recorded in chloroform-d or DMSO-d6 on a Mercury-300BB or INOVA-500 spectrometer and mass spectra on an Agilent LCMS system.

General Procedure of 6-nitro-quinoxalines 3.

A mixture of 4-nitrobenzene-1,2-diamine (10 mmol) and dione 2 (10 mmol) in ethanol (40 ml) was heated at reflux for 24-40 h. The mixture was cooled in an ice bath and the resulting solid was recrystallized from methanol gave 6-nitro-quinoxalines (3a-d) (85-90%).

General Procedure of 6-amino-quinoxalines 4.

6-Nitro-quinoxaline (3, 5 mmol) was hydrogenated in the presence of 5% Pd/C (50 mg) under at room temperature in ethanol (30 ml) for 6-10 h. After the reaction 2 ml DMSO was added to the mixture and filtered. The filtrate was poured into water (200 ml) and the precipitate was filtered to give 6-amino-quinoxaline (4a-d) (90-95%).

General Procedure of Quinoxalinylurea and Quinoxalinylthiourea Derivatives 5.

To a stirring solution of 4 (1.0 mmol) and triethylamine or diisopropylethylamine (3.0 mmol) in dichloromethane (20-30 ml), the corresponding acetyl chloride (1.5 mmol) or phenylisocyanate (1.5-2.0 mmol) or toluene sulfonyl chloride (1.5-2.5 mmol) was added. The mixture was maintained at room temperature for 12-48 h and the reaction monitored for completion by TLC. Upon consumption of the starting material (4) the solvent was removed and the residue was purified by flash column chromatography on a silica gel to yield the desired compounds.

General Procedure of Quinoxalinylurea Derivatives 6

Method A:

To a stirring solution of 4 (1.0 mmol) and diisopropylethylamine (3.0 mmol) in dichloromethane (20-30 ml) the corresponding isothiocyanate (1.5-2.0 mmol) was added. The mixture was stirred at room temperature for 24-48 h. Upon consumption of the starting material as determined by TLC, the reaction mixture was diluted with 20 mL hexanes. The resulting solid was filtered and the residue washed with $CH_2Cl_2$ (2×5 mL). The material was subsequently purified by flash column chromatography on a silica gel to yield the desired compounds.

Method B:

To a stirring solution of 4 (1.0 mmol) and diisopropylethylamine (3.0 mmol) in dichloromethane (10-20 mL), triphosgene (0.40 mmol) was added. The mixture was stirred at room temperature for 4-8 h and the corresponding secondary amine (2.0-3.0 mmol) was added. After stirring for an additional 8-12 h, the solvent was removed under vacuum and the residue was purified by flash column chromatography on a silica gel yield the desired compounds.

General Procedure of Quinoxalinylurea Derivatives 7

To a stirring solution of 4 (1.0 mmol) and diisopropylethylamine (3.0 mmol) in dichloromethane (20-30 ml) the corresponding isocyanate (1.5-2.0 mmol) was added. The mixture was maintained at room temperature for 24-48 h and reaction monitored for completion by TLC. Upon consumption of the starting material (4) the reaction mixture was diluted with 20 mL hexanes, filtered, the residue washed with $CH_2Cl_2$ (2×5 mL) and purified by flash column chromatography on a silica gel to yield the desired compounds.

Biological Assays of Compounds of Table 1

Cell Growth Inhibition Assay.

Human lung A549, human pancreatic AsPC1, human colorectal HT-29, human breast MDA-MB-231, human prostate PC3, human ovarian SKOV3, and human osteosarcoma U2OS tumor cell lines were cultured in basal media containing 10% FBS and maintained in a 37° C. incubator with 5% $CO_2$. All compounds were screened in 96 well microtiter plate format. In general, each cell line was plated at optimal assay density in 95 µl of propagation media in 96 well plates and incubated overnight. The next day, a standard alamar blue assay was performed (see below) on representative wells of each cell line for a $T_z$ calculation. Subsequently, cells were treated in duplicate with a 5 µl volume of either vehicle only, positive controls etoposide and taxol, or test compounds at 20 µM (highest soluble compound concentration). The treated cells were incubated for 72 h and then assayed for growth by alamar blue assay. Briefly, 10 µl of reagent was added to each well and the plates returned to 37° C. After 3 h, fluorescence at $544_{ex}/590_{em}$ was measured using a SpectraMax M5 (Molecular Devices) plate reader. Growth is represented as a percentage of the control cells that were treated with vehicle only and % growth inhibition was determined using the NCI algorithm: $T_z$=number of untreated cells at zero time, C=Number of control cells at 72 h time, and T=number of compound treated cells at 72 h time; $100*([T-T_z]/[C-T_z])$.

Caspase 3/7 Activation.

HeLa, MDA-MB-231 (4000 cells/well), and PC3 (2000 cells/well) cells were treated in 96 well plates with 7c at the indicated times. Caspase Glo reagent (Promega, Inc.) was added and luminescence was measured using a Spectramax M5 (Molecular Devices) plate reader after 1 hr. Raw luminescence values were normalized to alamar blue.

PARP Cleavage.

HeLa cells were treated with 7c for the indicated times. Samples were prepared by collecting media, trypsinizing cells, and centrifuging to obtain a combined cell pellet from all steps. Cells were lysed in RIPA buffer and protein content was subjected to SDS-PAGE. PARP cleavage was determined via Western blotting using anti-PARP antibody (Calbiochem #AM30).

Mcl-1 Dependent Apoptosis Assay.

HeLa cells overexpressing the inducible Bcl-xL and Bcl-2 inhibitor Bad3SA were induced with doxacyclin (Dox) for 3 hrs. Cells were then treated with various concentrations of 7c for 12 hrs. Cells were then fixed and stained with Hoechst dye and the number of condensed nuclei was counted for each treatment to determine percent death.

Studies on 13-197 (aka 7c)

A cell line designed to specifically monitor the activity of NF-κB in response to TNF-α was used for the screen. The compounds were screened at 20 µM, and their $IC_{50}$ values determined. The arrow points to the quinoxaline urea analog 13-197 (7c), a quinoxaline urea analog that inhibits TNF-α mediated NF-κB activation (FIGS. 1A and 1B). The molecular target of 13-197 in the NF-κB pathway was then determined.

Activation of NF-κB pathway by TNF-α leads to the nuclear translocation of NF-κB (p65). To explore if 13-197 inhibits the nuclear translocation of NF-κB, cells were treated with TNF-α in the presence and absence of 13-197. Nuclear NF-κB (p65) levels at indicated time points were determined by Western blot analyses. The cells were treated with 20 µM of 13-197 followed by 20 ng/mL of TNF-α. The cell lysates were fractionated at the indicated time points and the nuclear fractions were probed for NF-κB levels (p65). The bottom panel shows quantitation (n=3). (FIG. 1C). The results show that 13-197 inhibits TNF-α mediated nuclear translocation of NF-κB and is consistent with inhibition of transcription (FIG. 1B).

In the resting state IκBα sequesters NF-κB in the cytoplasm by masking its nuclear localization signal (NLS). Activation of the NF-κB pathway by TNF-α results in the phosphorylation, ubiquitination and degradation of IκBα, thus unmasking the NF-κB NLS. To determine if 13-197 inhibits the phosphorylation of IκBα, cells were treated with and without 13-197 followed by TNF-α. The phospho-IκBα levels in the cytoplasm (at the indicated time points) were determined by Western blot analyses. The NF-κB pathway was activated by TNF-α (20 ng/mL) in cells treated with and without 13-197 (20 μM). Cell lysates were generated at indicated times and probed for p-IκBα, total-IκBα and tubulin. (FIG. 1D). The results indicate 13-197 partially inhibits IκBα phosphorylation at the early time points (5 and 10 min). More importantly, we observe complete inhibition of IκBα phosphorylation at the later time points (60 and 120 mins).

IκBα is phosphorylated by IKKβ in response to TNF-α stimulation. The IκBα-NFκB complex is a better substrate for IKKβ compared to IκBα alone ($K_m$=2.2 μM vs. 1.4 μM and 5-fold change in $V_{max}$). IκBα is also a target gene of NF-κB and this serves as one of the feedback mechanism to shut down the NF-κB pathway. The partial inhibition of IκBα phosphorylation at the early time points and the completed inhibition of the newly formed IκBα phosphorylation, could be explained if 13-197 targets the IκBα-NFκB interface. To test this hypothesis we conducted reciprocal immunoprecipitation (IP) and immunoblotting (IB) at an early (5 min) and a late (120 min) time point post TNF-α stimulation. Cell lysates were generated at the indicated times post TNF-α (20 ng/mL) stimulation with and without 13-197 (20 μM). The lysates were subjected to reciprocal IP-IB with NF-κB (p65) and IκBα antibodies (FIG. 1E). The results showed no change in the relative levels of NF-κB pulled down by IκB and vice versa at either time points suggesting 13-197 does not inhibit the IκBα-NFκB complex.

In response to TNF-α stimulation IκBα is phosphorylated by the kinase IKKβ, therefore we next evaluated if 13-197 inhibits IKKβ. An in vitro ELISA assay with full length IKKβ showed that 13-197 inhibits IKKβ with an $IC_{50}$ value of about 15 μM (FIG. 1F). This indicates that 13-197 inhibits IKKβ, however it does not fully explain the results in FIG. 1D. Also as a general rule the $IC_{50}$ values are lower by at least an order of magnitude for in vitro assays compared to cell-based assays. With 13-197 we see the comparable effect as the cell-based $IC_{50}$ value is ~10 μM (FIG. 1B).

Figure 1G:
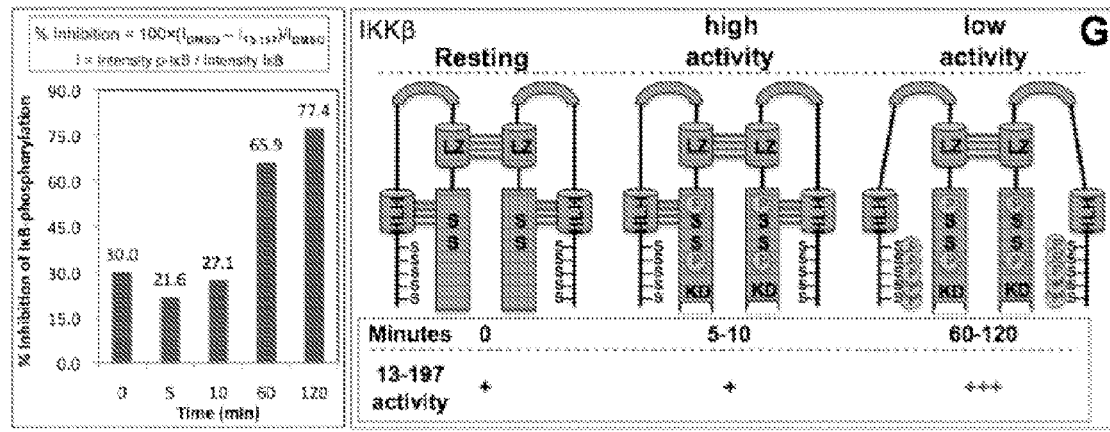
Figure 2:
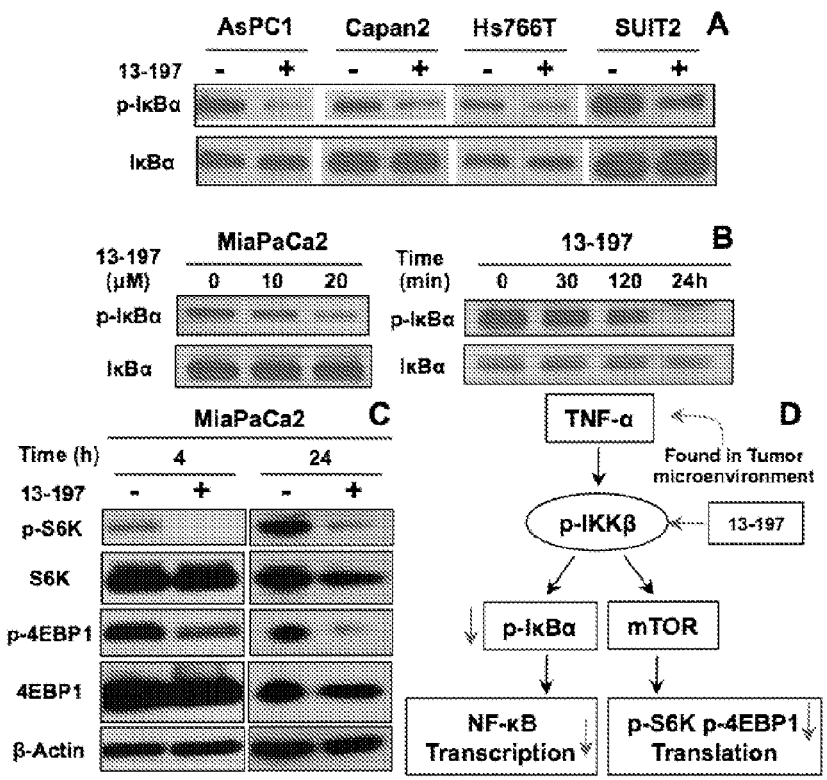
FIG. 2. (A) Pancreatic cancer cell lines were treated with 20 μM 13-197 for 2 h and the lysates were probed for p-IκBα and total IκBα. (B) (left) MiaPaCa2 cells were treated with 13-197 (0, 10 and 20 μM) for 2 h and at 20 μM (right) for the indicated time. (C) MiaPaCa2 cells were treated with 20 μM 13-197 for 4 h and 24 h. The cell lysates were probed for p-S6K and p-eIF4EBP1. (D) A model that suggests the molecular target for 13-197 is the constitutively active IKKβ.
Figure 3:
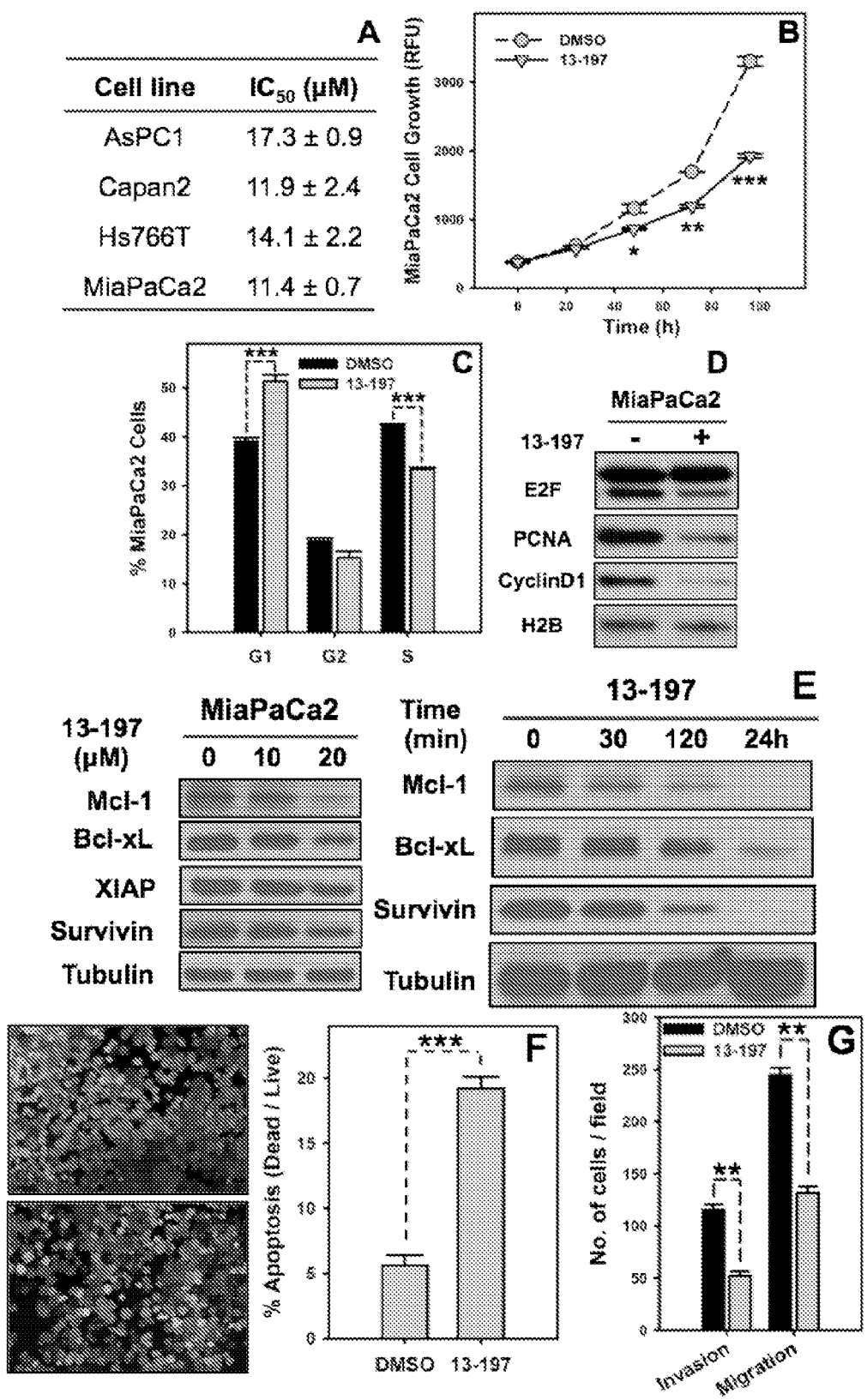
FIG. 3. (A) Pancreatic cells were treated with 13-197 for 72 h. IC₅₀ values determined through curve fitting (n=2). (B) MiaPaCa2 cells treated with 11 μM of 13-197 and viability measured at indicated times. *P<0.05, P<0.005, *P<0.005. (C) MiaPaCa2 cells were treated with 11 μM 13-197 for 24 h followed by cell cycle analyses (n=3). (D) Cell lysates were probed for cell cycle markers. (E) Dose- and time-dependent effects of 13-197 on the levels of anti apoptotic proteins Mcl-1, Bcl-xL, XIAP and Survivin in MiaPaCa2 cells. MiaPaCa2 cells were treated with 13-197 at the indicated doses 2 h (left panel). Cells were treated with 20 μM the cell lysates were generated probed at the indicated time points (right panel).
Figure 4:
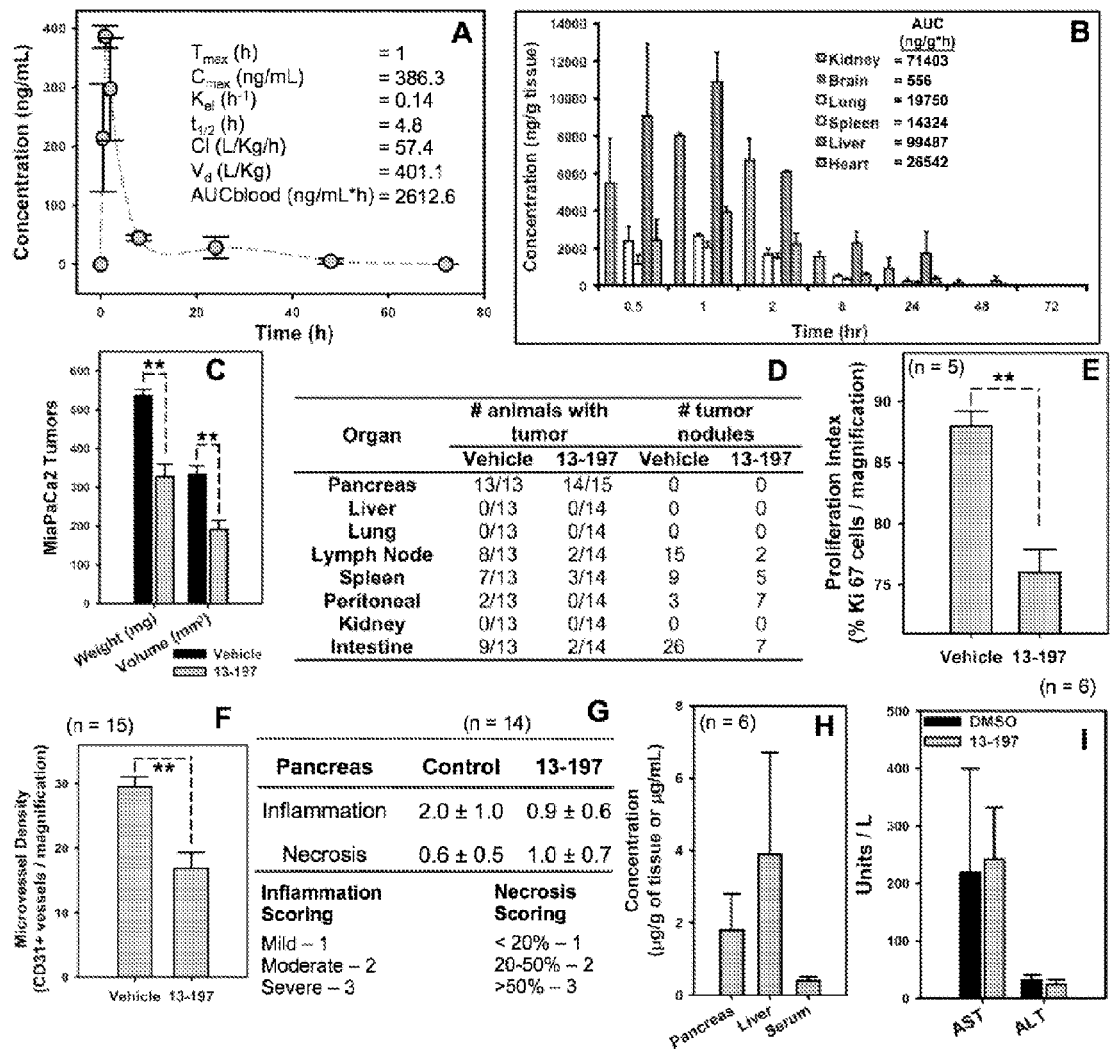
FIG. 4. (A) Plasma concentration time profile of 13-197 after oral administration in mice. 13-197 concentrations in plasma are expressed as mean values (±SEM) at the 7 sampling times (0.5, 1, 2, 8, 24, 48, and 72 h; n=3). Non-compartmental pharmacokinetic parameters are summarized as an inset in the figure. (B) Biodistribution of 13-197 in kidney, brain, lung, spleen, liver, and heart following oral administration of 150 mg/kg in mice (data is expressed as mean±SEM, n=3). The area under the curve (AUC) for each tissue is described in the inset. (C) Nude mice with orthotopic pancreatic tumors were treated with 13-197 (150 mg/Kg) or vehicle orally daily for 30 days. (D) Table describes the number of animals with tumors and number of tumor nodules found in various organs (E) Ki67 staining as a measure of proliferation index in tumor tissue (F) CD31+ staining as a measure of microvessel density. (G) Inflammation and Necrosis scored (blind) by a pathologist in the tumor tissue (H) 13-197 levels measured in the pancreas, liver and serum 18 h after the last treatment (I) Liver enzymes (AST and ALT) measured at the end of the study. **P<0.05

IKKβ is regulated by a plethora of phosphorylation events. TNF-α stimulation induces rapid phosphorylation of Ser177 and Ser181 residues in the activation loop (T-loop). The T-loop phosphorylated IKKβ is in a high-active state and rapidly phosphorylates IκBα (FIG. 1D-5 and 10 min lanes). Concurrently, the T-loop phosphorylated IKKβ undergoes autophosphorylation at C-terminus serine residues which result in a low-active hyperphosphorylated form of IKKβ. If 13-197 preferentially inhibits the hyperphosphorylated form of IKKβ it would explain the results observed in FIG. 1D. This model also agrees with the results in FIG. 1F which shows inhibition of the full length unactivated form of IKKβ. FIG. 1G pictorially depict a proposed model and a potential target for 13-197.

The T-loop phosphorylated form of IKKβ (p-IKKβ) is found in ~50% of surgical tumor specimens and in ~10% of normal tissues. Also a perfect correlation between the presence of TNFα, p-IKKβ and p-IκBα was observed. Since NF-κB is constitutively active in pancreatic cancer (PC) we hypothesize that 13-197 will inhibit the constitutively active form of IKKβ in pancreatic cancers. To test this we subjected a panel of pancreatic cancer cell lines to 13-197 and probed the lysates for p-IκBα levels (FIGS. 2A and 2B). (A) Pancreatic cancer cell lines were treated with 20 μM 13-197 for 2 h and the lysates were probed for p-IκBα. (B) (left) MiaPaCa2 cells were treated with 13-197 (0, 10 and 20 μM) for 2 h and at 20 μM for the indicated times (right). 13-197 robustly inhibits phosphorylation of IκBα in PC cell lines both in a dose- and time-dependent manner.

TNF-α stimulation regulates transcription via the p-IKKβ/p-IκBα/NF-κB axis. It also regulates translation via the p-IKKβ/mTOR/p-S6K/p-eIF4EBP axis. We speculated that if the IKKβ node is activated in pancreatic cancer we should also see inhibition of p-S6K and p-eIF4EBP. Indeed we observed decreased p-S6K and p-4EBP1 in MiaPaCa2 cells treated with 13-197 (FIG. 2C). (C) MiaPaCa2 cells were treated with 20 μM 13-197 for 4 h and 24 h. The cell lysates were probed for p-S6K and p-eIF4EBP1. In summary the data in FIGS. 2A-C suggests that 13-197 targets a constitutively active form of IKKβ in pancreatic cancer cell lines (FIG. 2D).

We next explored if inhibition of constitutively active IKKβ by 13-197 results in the inhibition of pancreatic cancer cell growth. In a typical experiment pancreatic cancer cells were subjected to increasing doses of 13-197 (FIG. 3A). (A) Pancreatic cells were treated with 13-197 for 72 h. $IC_{50}$ values determined through curve fitting (n=2). In a second experiment MiaPaCa2 cells were incubated with 13-197 (at $IC_{50}$) and the cell growth was monitored over time for 96 h (FIG. 3B). (B) MiaPaCa2 cells treated with 11 μM of 13-197 and viability measured at indicated times. *P<0.05, P<0.005, *P<0.005. The viability of the cells at the end of these studies was determined by the AlamarBlue dye. The results demonstrate that 13-197 inhibits pancreatic cancer cell growth both in a dose- (low-μM $IC_{50}$ values) and in a time-dependent manner. To determine if the growth inhibition induced by 13-197 is a result of cell cycle arrest, MiaPaCa2 cells were treated with 13-197 and subjected cell cycle analysis. Cells treated with 13-197 arrested in the G1 phase (FIG. 3C). (C) MiaPaCa2 cells were treated with 11 μM 13-197 for 24 h followed by cell cycle analyses (n=3). Consistent with the G1 arrest we observe reduced levels of the corresponding cell cycle markers E2F, PCNA and Cyclin D1 (FIG. 3D). Together the data in FIGS. 3A-D demonstrates that 13-197 inhibits pancreatic cancer cell growth by inducing G1 arrest of cells.

Next we probed the effect of 13-197 on apoptosis related proteins. Mcl-1 and Bcl-xL are antiapoptotic proteins that sequester the proapoptotic proteins (Bax/Bak). XIAP and Survivin belong to the IAP family and are inhibitors of caspase activation. (E) Dose- and time-dependent effects of 13-197 on the levels of anti apoptotic proteins Mcl-1, Bcl-xL, XIAP and Survivin in MiaPaCa2 cells. MiaPaCa2 cells were treated with 13-197 at the indicated doses 2 h (left panel). Cells were treated with 20 μM the cell lysates were generated probed at the indicated time points (right panel). The dose response study (2 h) shows a significant decrease in the Mcl-1 levels compared to the other proteins (FIG. 3E, left panel). However, longer incubation times at 20 μM shows a decrease in all proteins (FIG. 3E, right panel). The distinct kinetics (Mcl-1 vs Bcl-xL/XIAP/Survivin) suggests that Mcl-1 could be down regulated by IKKβ directly while the others are down regulated by the inhibition of NF-κB activation. In all the data shows that 13-197 down regulates antiapoptotic proteins both in a dose- and time-dependent manner.

MiaPaCa2 cells were subjected to 11 μM 13-197 for 24 h and apoptosis was measured by the live/dead cellular assay. Cells treated with 13-197 showed a 4-fold increase in percentage of apoptotic cells when compared to untreated cells (FIG. 3F). This is consistent with the down regulation of antiapoptotic proteins (FIG. 3E).

NF-κB regulates the expression of several genes such as IL-8, VEGF, ICAM1 and MMP-9 that are implicated in angiogenesis, invasion and metastasis. Invasion of cells through matrigel coated microporous polycarbonate membrane was measured in the presence and absence of 13-197 (n=3). Transwell serum driven migration of cells in the presence and absence of 13-197 was measured after a 24 h incubation. (n=3). P<0.005 and *P<0.0005. We observed that 13-197 inhibited both the invasion and migration of MiaPaCa2 cells by about 50% (FIG. 3G). This suggests that 13-197 has the potential to not only inhibit growth of tumors but also inhibit metastasis.

In summary cellular studies with 13-197 suggests that it targets the "disease state" of IKKβ (T-loop and C-terminus phosphorylated). In pancreatic cancer cells 13-197 targets the constitutively activated IKKβ as it down regulates transcription via the IKKβ/IκBα/NF-κB axis and perturbs translation through the IKKβ/mTOR/S6K-eIF4EBP axis. 13-197 also down regulates antiapoptotic proteins. As a consequence 13-197 inhibits cell growth and induces apoptosis in MiaPaCa2 cells.

PK difficulties account for more than 50% of drug development failures preventing new chemical entities (NCEs) from reaching the market, whereas toxicity issues and lack of efficacy account for only 30% of development failures. As a result, in addition to paying attention to the traditional concern of attaining potency and selectivity towards the biological target of interest, PK considerations have been moved to early stages of drug discovery, a significant paradigm shift in the pharmaceutical industry. Along these lines we determined the PK parameters for our NCE 13-197.

Lipinski's rule of five serves as a guide to determine if compounds will be orally bioavailable. Analysis of 13-197 suggested that it would be orally available. 13-197 was formulated in cremaphor EL a commonly used excipient in drugs for pharmacokinetic (PK) and tissue distribution studies. A mass spectrometry method was established to determine 13-197 levels in plasma and tissue. Mice were dosed at 150 mg/Kg orally and sacrificed at indicated time points. 13-197 levels in blood and various tissue samples were determined by mass spectrometry (FIGS. 4A and 4B). The PK properties of 13-197 are described as an inset in FIG. 4A and the tissue levels as an inset in FIG. 4B. The results show that 13-197 is orally available, has an excellent distribution (large $V_d$) and is primarily cleared through the liver and the kidney.

Once we established that 13-197 is orally available, MiaPaca2 cells were orthotopically placed in the pancreas of nude mice. The mice were allowed to heal after surgery and the tumors were allowed to grow for 2 weeks at which time they were palpable. The tumor bearing mice were randomized and half the animals were treated orally with 13-197 at 150 mg/Kg in cremaphor daily. At the end of 30 days the mice were sacrificed and the tumors weights and volumes were measured (FIG. 4C). We observed about 50% reduction in both the tumor weight and volume in the 13-197 treated animals compared to vehicle treated animals. We also found fewer tumor nodules in other organs of 13-197 treated animals compared to vehicle treated animals (FIG. 4D). These result are consistent with our cellular data suggest inhibition of tumor growth and metastases by 13-197. Proliferation index and microvessel density are measures of the number of cells dividing in the tumor and angiogenesis indicators respectively. We observe a reduction of both in 13-197 treated tumors compared to vehicle controls (FIGS. 4E and 4F). The tumor tissue was scored and the results indicate decreased inflammation and increased necrosis in the 13-197 treated mice (FIG. 4G). These results are consistent with the inhibition of NF-κB. We also determined the 13-197 levels in the pancreas, liver and serum at the end of the study (FIG. 4H). Consistent with our PK data the highest drug levels found in the liver. Since 13-197 is primarily cleared by the liver we measured the levels of aspartate aminotransferase (AST) and alanine aminotransferase (ALT) which are biochemical markers of the liver toxicity in 13-197 and vehicle treated mice. We did not observe a difference in the ALT or AST levels in 13-197 treated mice when compared vehicle treated mice indicating the absence of liver toxicity (FIG. 4I). We also conducted a macroscopic examination of the organs and found no obvious toxicity in the 13-197 treated animals. In summary our studies in animals show that 13-197 is orally available with excellent distribution (high $V_d$). It inhibits tumor growth and metastasis in mice bearing pancreatic tumors with no obvious toxicity.

Figure 7:
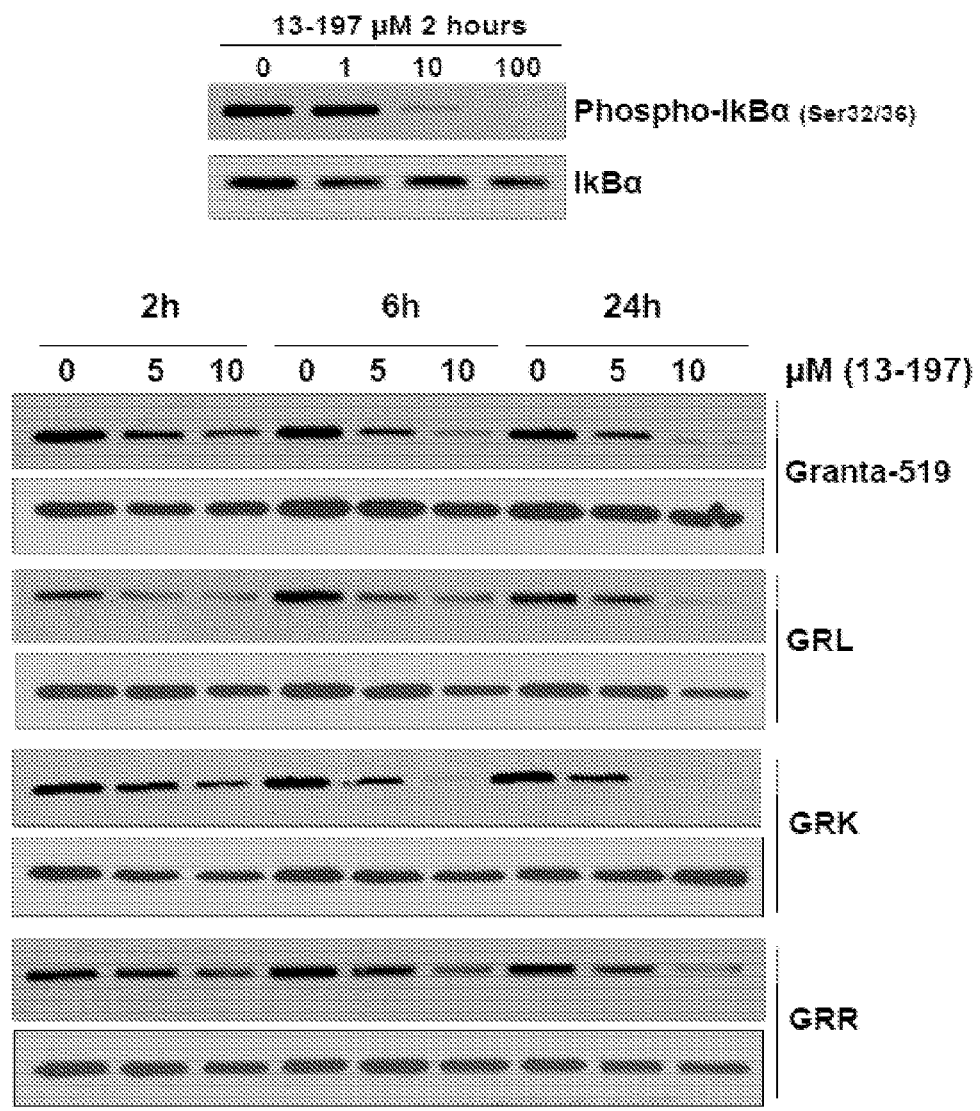
FIG. 7 shows the effect of 13-197 on the IkBα phosphorylation in the therapy-resistant MCL cells.

The effect of 13-197 on the IκBα phosphorylation in therapy-resistant MCL cells was assessed. 5×10$^6$ each MCL cells were cultured in RPMI media containing vehicle (DMSO) or indicated concentration of 13-197 for different time point (2-24 hours). After time incubation, cells were harvested and whole cell lysate was prepared. 20-50 μg of total protein from whole cell lysate was subjected to western blot for the expression of IκBα phosphorylation. FIG. 7A shows western blot results for IκBα phosphorylation by 13-197 in Granta-519 parental (GP) cells in a dose-dependent manner. FIG. 7B indicates phosphorylation status of IκBα by 13-197 in GP, GRL, GRK and GRR MCL cells in time- and dose-dependent manner. Total IκBα was used as an internal control in these experiments.

Figure 8:
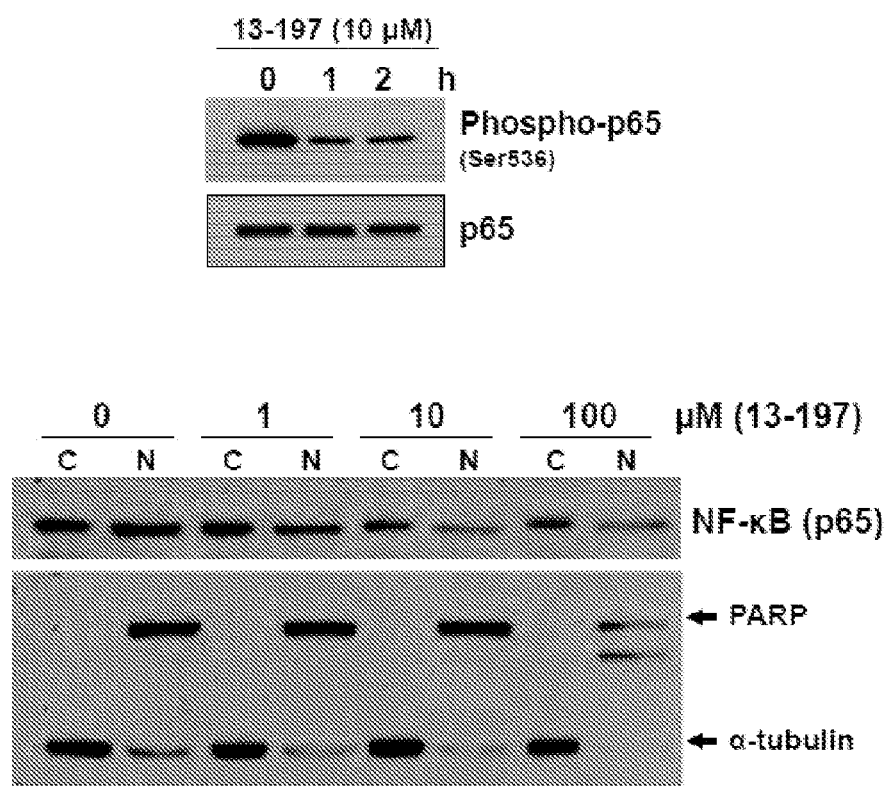
FIG. 8 shows effect of 13-197 on the down-regulation of the NF-κB (p65) phosphorylation and their nuclear translocation in the therapy-resistant MCL cell lines.

The effect of 13-197 on the down-regulation of the NF-κB (p65) phosphorylation and their nuclear translocation in the therapy-resistant MCL cell lines was assessed. 5×10$^6$ each MCL cells were cultured in RPMI media containing vehicle (DMSO) or indicated concentrations (1-100 μM) of 13-197 for 1 or 2 hours. After time incubation, cells were harvested and whole cell lysate or cytoplasmic/nuclear fraction was prepared. 20-50 μg of total protein from whole cell lysate or cytoplasmic/nuclear fractionated lysate was subjected to western blot for the expression of NF-κB (p65) phosphorylation and their nuclear translocation. FIG. 8A shows phosphorylation status of NF-κB (p65) by 13-197 in Granta-519 cells in a time-dependent fashion. FIG. 8B shows western blot results for NF-κB nuclear translocation by 13-197 in Granta-519 MCL cells in a dose-dependent manner after cytoplasmic and nuclear fractionation of the cells. PARP-1 and α-tubulin were also detected to confirm cytoplasmic and nuclear fractionation of proteins.

Figure 9:
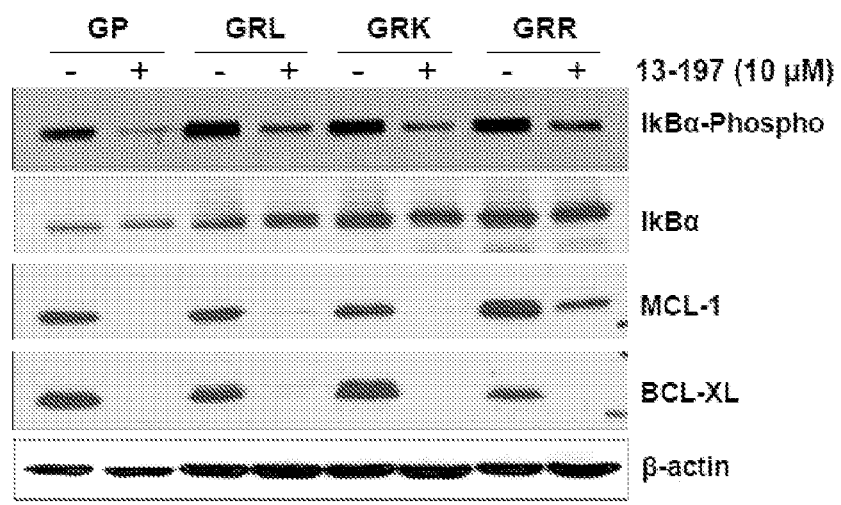
FIG. 9 (top) shows the effect of 13-197 on the down-regulation of antiapoptotic proteins and (bottom) down regulation of cyclin D1 (a NF-κB target) in therapy-resistant MCL cells.
Figure 9:
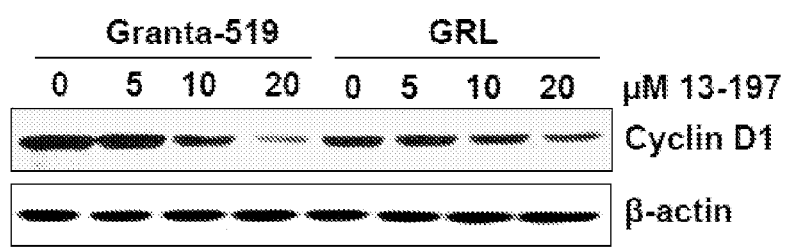

The effect of 13-197 on the down-regulation of the NF-κB target in the therapy-resistant MCL cells was assessed. 5×10$^6$ each MCL cells were cultured in RPMI media containing vehicle (DMSO) or indicated concentration of 13-197 for 24 hours. After incubation time, cells were harvested and whole cell lysate was prepared. ~50 μg of total protein from whole cell lysate was subjected to western blot for the expression of NF-κB target molecules. FIG. 9A shows status of IκBα phosphorylation, MCL-1 and BCL-XL in 13-197 (10 μM) treated-Granta-519 (GP), -GRL, -GRK and -GRR MCL cells. FIG. 9B represents expression level of cyclin D1 in 13-197 treated- Granta-519 (GP) and GRL MCL cells in a dose-dependent manner. β-actin was used as an internal control in the each experiment.

Figure 10:
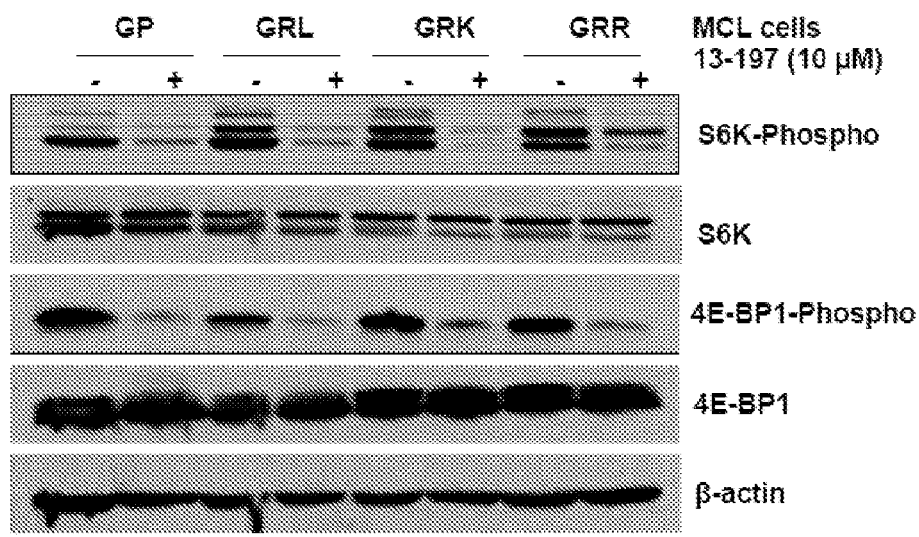
FIG. 10 shows the effect of 13-197 on the phosphorylation of the mTOR target molecules S6K and eIF4EBP1 in the therapy-resistant MCL cells.
Figure 11:
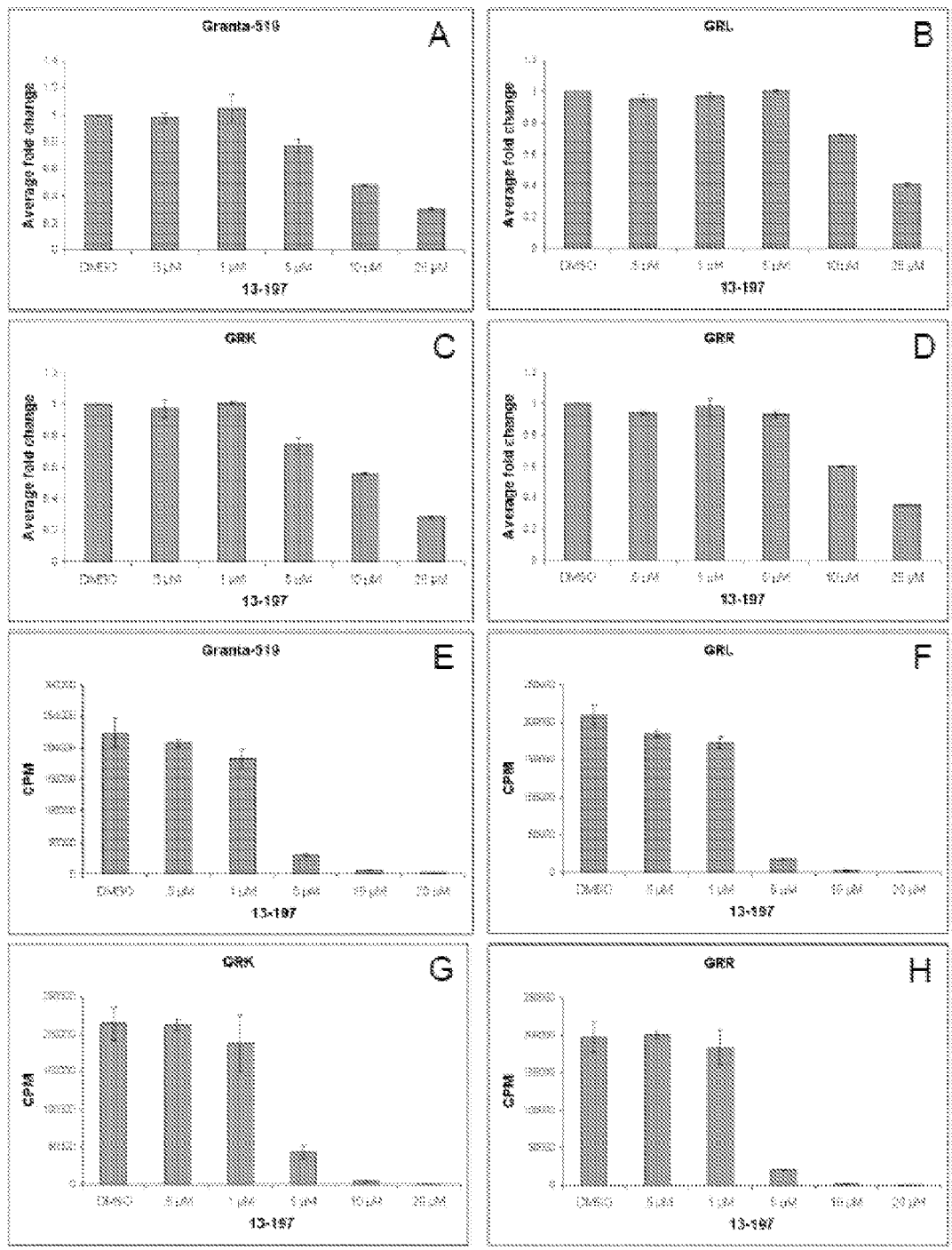
FIG. 11 shows the effect of 13-197 on therapy-resistant MCL cells growth/proliferation in vitro.

The effect of 13-197 on the down-regulation of the mTOR target molecules in the therapy-resistant MCL cells was assessed. $5\times10^6$ different MCL cells were cultured in RPMI media containing vehicle (DMSO) or 13-197 (10 µM) for 24 hours. After incubation time, cells were harvested and whole cell lysate was prepared. 50 µg of total protein from whole cell lysate was subjected to western blot for the expression of phosphorylation status of mTOR pathway molecules include S6K and 4E-BP1. β-actin was used as an internal control in the experiment. GP indicates 'Granta-519'. The results are shown in FIG. 10

The effect of 13-197 on therapy-resistant MCL cells growth/proliferation in vitro was assessed. Therapy-resistant MCL cells [Granta-519 parental (GP); GRL, derived from liver; GRK, derived from kidney and GRR, derived from lungs] MCL cells (10,000) were cultured in RPMI media containing 0.5, 1.0, 5.0, 10 and 20 µM 13-197 compound in 96-well plates for 48 hours. FIG. 11A-11D: MTT reagent was added 2 hours before cell harvest. MTT developed color was read using a microplate reader at 570 nm Fold change was calculated with respect to absorbance exhibited by vehicle (DMSO)-treated cells. The values represent the means±SD from four wells of at least three independent experiments. FIG. 11E-11H: $^3$[H]-thymidine (0.5 µCi) was added 15 hours before harvesting the cells, and incorporated radioactivity was determined using a scintillation counter. The values represent the means±SD from triplicate wells of at least three independent experiments.

Figure 12:
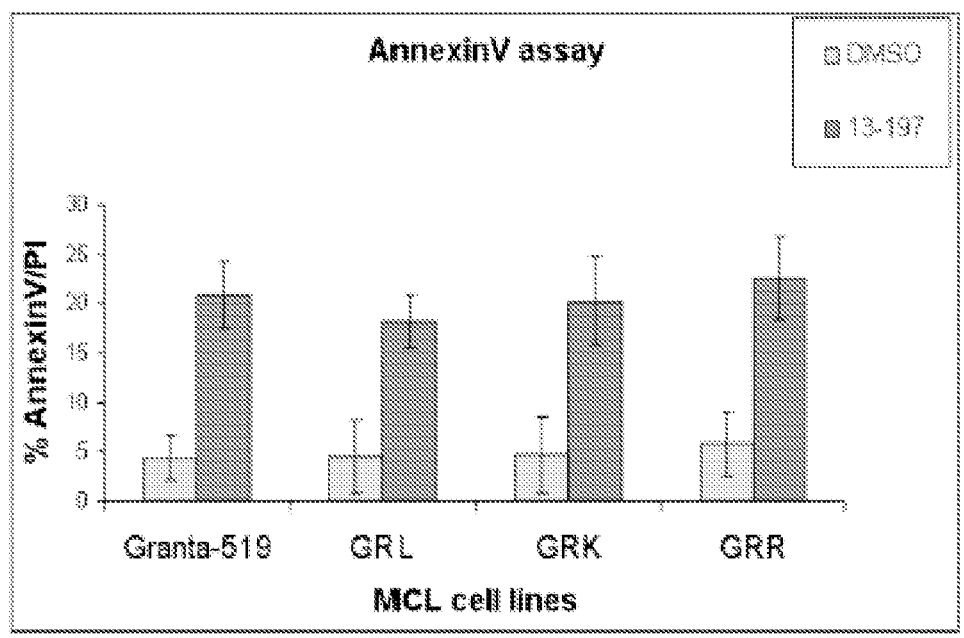
FIG. 12 shows the effect of 13-197 on MCL cells apoptosis.

The effect of 13-197 on MCL cells apoptosis was assessed. AnnexinV-FITC apoptosis detection assay was used to access percent of cells undergoing apoptosis in granta 519 parental, GRL, GRK and GRR MCL cell lines following treatment with 10 µM 13-197 for 48 hours. The percent of cells undergoing apoptosis indicate annexin and propidium iodide (PI) positive, as shown in FIG. 12. The values represent the means±SD of three separate experiments.

Figure 13:
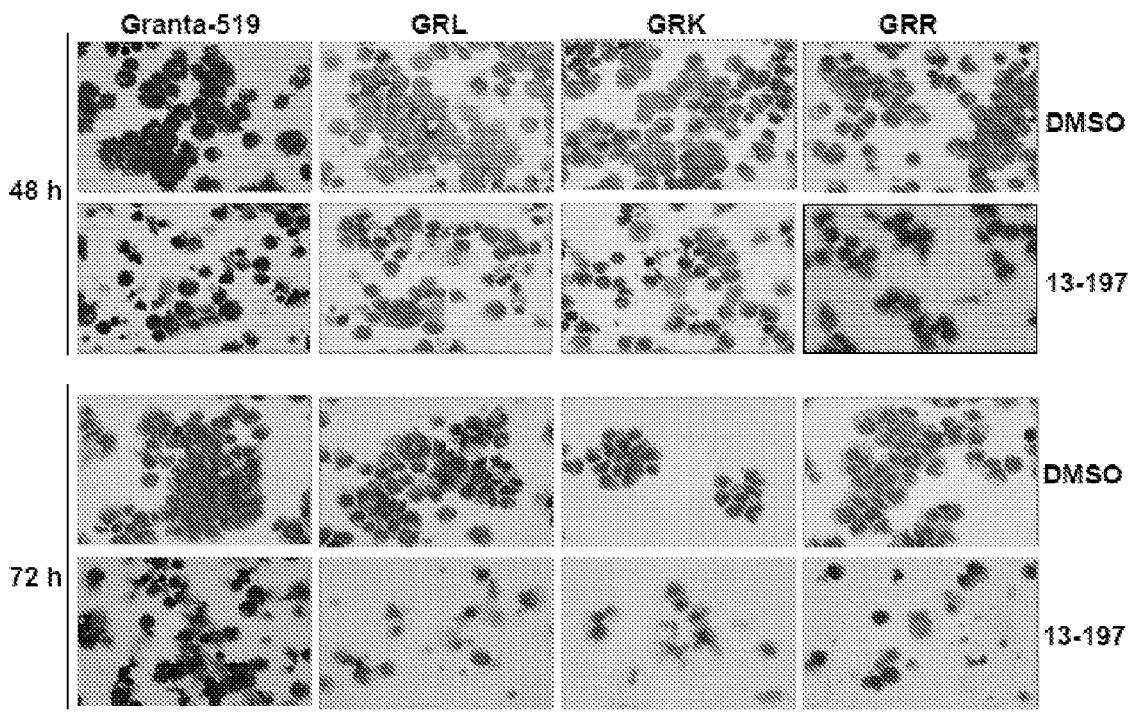
FIG. 13 shows the cytomorphology of Wright-Giemsa stained MCL cells following treatment with 13-197.

The cytomorphology of Wright-Giemsa stained MCL cells following treatment with 13-197 was assessed. Exponentially growing therapy-resistant MCL cells were treated with 13-197 (10 µM) for 48 and 72 hours. After treatment incubation cells were processed for Giemsa staining followed by cyto-spin. The cells were observed under the bright field microscope and images were captured at 40× magnification, as shown in FIG. 13.

REFERENCES

Delhase, M., Hayakawa, M., Chen, Y. & Karin, M. Positive and negative regulation of IkappaB kinase activity through IKKbeta subunit phosphorylation. *Science* 284, 309-313 (1999).

Hacker, H. & Karin, M. Regulation and function of IKK and IKK-related kinases. *Sci STKE* 2006, re 13 (2006).

Chiang, C. W., Liu, W. K., Chiang, C. W. & Chou, C. K. Phosphorylation-dependent association of the G4-1/G5PR regulatory subunit with IKKbeta negatively modulates NF-kappaB activation through recruitment of protein phosphatase 5. *Biochem J* 433, 187-196 (2011).

Lee, D. F. et al. IKK beta suppression of TSC1 links inflammation and tumor angiogenesis via the mTOR pathway. *Cell* 130, 440-455 (2007).

Bjellqvist, B. et al. The focusing positions of polypeptides in immobilized pH gradients can be predicted from their amino acid sequences. *Electrophoresis* 14, 1023-1031 (1993).

Druker, B. J. et al. Effects of a selective inhibitor of the Abl tyrosine kinase on the growth of Bcr-Abl positive cells. *Nat Med* 2, 561-566 (1996).

Sen, R. & Baltimore, D. Inducibility of kappa immunoglobulin enhancer-binding protein Nf-kappa B by a posttranslational mechanism. *Cell* 47, 921-928 (1986).

Baldwin, A. S., Jr. The NF-kappa B and I kappa B proteins: new discoveries and insights. *Annu Rev Immunol* 14, 649-683 (1996).

Miyamoto, S., Chiao, P. J. & Verma, I. M. Enhanced I kappa B alpha degradation is responsible for constitutive NF-kappa B activity in mature murine B-cell lines. *Mol Cell Biol* 14, 3276-3282 (1994).

Conti, L. et al. Induction of relA(p65) and I kappa B alpha subunit expression during differentiation of human peripheral blood monocytes to macrophages. *Cell Growth Differ* 8, 435-442 (1997).

Farrow, B. & Evers, B. M. Inflammation and the development of pancreatic cancer. *Surg Oncol* 10, 153-169 (2002).

Aggarwal, B. B. Nuclear factor-kappaB: the enemy within. *Cancer Cell* 6, 203-208 (2004).

Wang, W. et al. The nuclear factor-kappa B RelA transcription factor is constitutively activated in human pancreatic adenocarcinoma cells. *Clin Cancer Res* 5, 119-127 (1999).

Chandler, N. M., Canete, J. J. & Callery, M. P. Increased expression of NF-kappa B subunits in human pancreatic cancer cells. *J Surg Res* 118, 9-14 (2004).

Weichert, W. et al. High expression of RelA/p65 is associated with activation of nuclear factor-kappaB-dependent signaling in pancreatic cancer and marks a patient population with poor prognosis. *Br J Cancer* 97, 523-530 (2007).

Cascinu, S. et al. COX-2 and NF-κB overexpression is common in pancreatic cancer but does not predict for COX-2 inhibitors activity in combination with gemcitabine and oxaliplatin. *Am J Clin Oncol* 30, 526-530 (2007).

Pan, X. et al. Nuclear factor-kappaB p65/relA silencing induces apoptosis and increases gemcitabine effectiveness in a subset of pancreatic cancer cells. *Clin Cancer Res* 14, 8143-8151 (2008).

Kong, R. et al. Downregulation of nuclear factor-kappaB p65 subunit by small interfering RNA synergizes with gemcitabine to inhibit the growth of pancreatic cancer. *Cancer Lett* 291, 90-98 (2010).

Fujioka, S. et al. Function of nuclear factor kappaB in pancreatic cancer metastasis. *Clin Cancer Res* 9, 346-354 (2003).

Mercurio, F. et al. IKK-1 and IKK-2: cytokine-activated IkappaB kinases essential for NF-kappaB activation. *Science* 278, 860-866 (1997).

Zandi, E., Chen, Y. & Karin, M. Direct phosphorylation of IkappaB by IKKalpha and IKKbeta: discrimination between free and NF-kappaB-bound substrate. *Science* 281, 1360-1363 (1998).

Darzynkiewicz, Z., Gong, J., Juan, G., Ardelt, B. & Traganos, F. Cytometry of cyclin proteins. *Cytometry* 25, 1-13 (1996).

Salvesen, G. S. & Abrams, J. M. Caspase activation—stepping on the gas or releasing the brakes? Lessons from humans and flies. *Oncogene* 23, 2774-2784 (2004).

Gilmore, T. D. Introduction to NF-kappaB: players, pathways, perspectives. *Oncogene* 25, 6680-6684 (2006).

Cheng, A. et al. Computation of the physio-chemical properties and data mining of large molecular collections. *J Comput Chem* 23, 172-183 (2002).

Clark, D. E. & Grootenhuis, P. D. Progress in computational methods for the prediction of ADMET properties. *Curr Opin Drug Discov Devel* 5, 382-390 (2002).

Lipinski, C. A., Lombardo, F., Dominy, B. W. & Feeney, P. J. Experimental and computational approaches to estimate solubility and permeability in drug discovery and development settings. *Adv Drug Deliv Rev* 46, 3-26 (2001).

Morikane, K. et al. Organ-specific pancreatic tumor growth properties and tumor immunity. *Cancer Immunol Immunother* 47, 287-296 (1999).

van Diest, P. J., van der Wall, E. & Baak, J. P. Prognostic value of proliferation in invasive breast cancer: a review. *J Clin Pathol* 57, 675-681 (2004).

Weidner, N. Current pathologic methods for measuring intratumoral microvessel density within breast carcinoma and other solid tumors. *Breast Cancer Res Treat* 36, 169-180 (1995).

De Ritis, F., Coltorti, M. & Giusti, G. An enzymic test for the diagnosis of viral hepatitis; the transaminase serum activities. *Clin Chim Acta* 2, 70-74 (1957).

Chen, Q. et al. 2,3-Substituted quinoxalin-6-amine analogs as antiproliferatives: a structure-activity relationship study. *Bioorg Med Chem Lett* 21, 1929-1932 (2011).

What is claimed is:

1. A compound having a structure of formula (I)

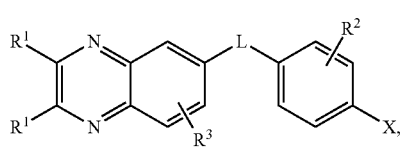

(I)

wherein each $R^1$ is independently heteroaryl, aryl, or alkyl;

L is selected from $-NHC(O)NH-$, $-NHC(O)CH_2-$,

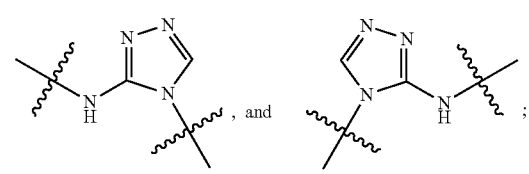 [SMILES: *Nc1nncn1* ; *Nc1nncn1*]

, and

X is halo, alkyl, alkoxy, aryl, $CO_2$alkyl, COalkyl, or haloalkyl;

$R^2$ is H, alkyl, alkoxy, $CO_2$alkyl, COalkyl, or haloalkyl; and $R^3$ is H, alkyl, or alkoxy;

or a salt thereof.

2. The compound of claim 1, wherein each $R^1$ is independently selected from furanyl, thiophenyl, pyridinyl, and phenyl.

3. The compound of claim 1, wherein at least one $R^1$ is methyl, ethyl, propyl, or isopropyl.

4. The compound of claim 1, wherein L is

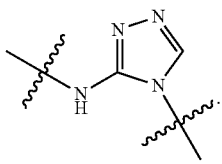 [SMILES: *Nc1nncn1*]

5. The compound of claim 1, wherein L is

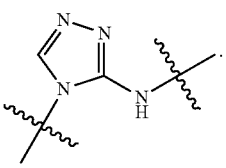 [SMILES: *Nc1nncn1*]

6. The compound of claim 1, wherein X is alkoxy.

7. The compound of claim 1, wherein X is $CF_3$, $CHF_2$, $CH_2F$, $CCl_3$, $CHCl_2$, $CH_2Cl$, $CBr_3$, $CHBr_2$, or $CH_2Br$.

8. The compound of claim 1, wherein $R^2$ is alkyl.

9. The compound of claim 1, wherein $R^2$ is $CF_3$, $CHF_2$, $CH_2F$, $CCl_3$, $CHCl_2$, $CH_2Cl$, $CBr_3$, $CHBr_2$, or $CH_2Br$.

10. A method of decreasing inhibitor of kappa B kinase β (IKKβ) activity in a cell comprising contacting the cell with the compound of claim 1 in an amount effective to decrease activity of IKKβ.

11. The method of claim 10, wherein the compound has a structure:

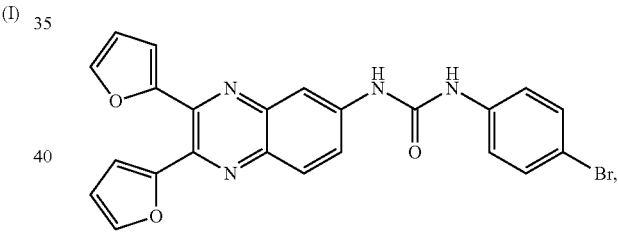

or a salt thereof.

12. A method of inhibiting nuclear factor kappa Kβ(NFκB) signaling pathway in a cell comprising contacting the cell with the compound of claim 1 in an amount effective to inhibit the NFκB signaling pathway.

13. The method of claim 12, wherein the compound has a structure:

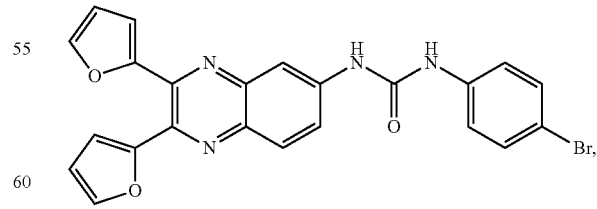

or a salt thereof.

14. A method of inhibiting mammalian target of rapamycin (mTOR) signaling pathway in a cell comprising contacting the cell with the compound of claim 1 in an amount effective to inhibit the mTOR signaling pathway.

15. The method of claim 14, wherein the compound has a structure:
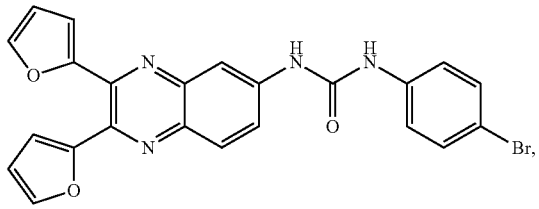 [SMILES: O=C(Nc1ccc(Br)cc1)Nc1ccc2nc(-c3ccco3)c(-c3ccco3)nc2c1]
or a salt thereof.
16. A compound selected from the group consisting of:
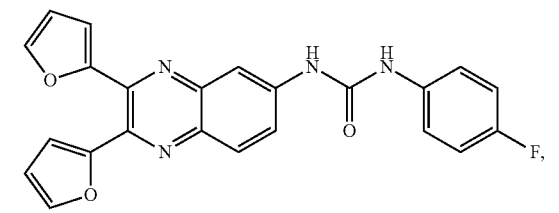
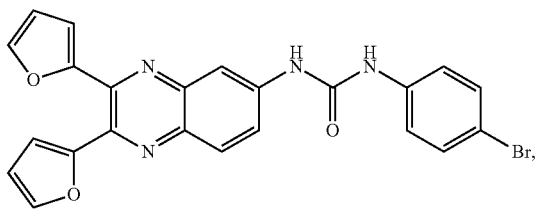 [SMILES: O=C(Nc1ccc(Br)cc1)Nc1ccc2nc(-c3ccco3)c(-c3ccco3)nc2c1]
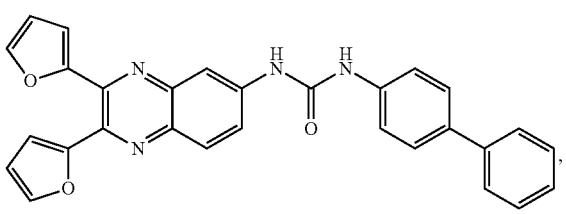
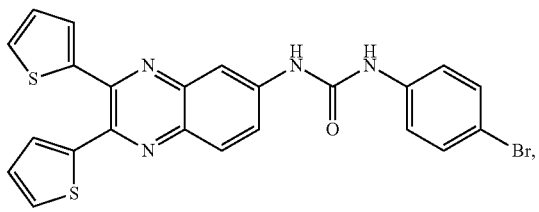 [SMILES: O=C(Nc1ccc(Br)cc1)Nc1ccc2nc(-c3ccco3)c(-c3ccco3)nc2c1]
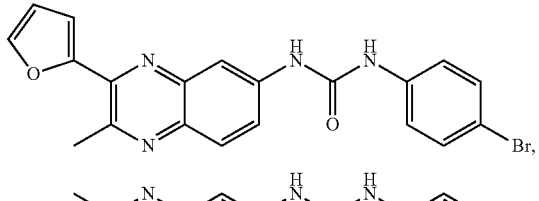
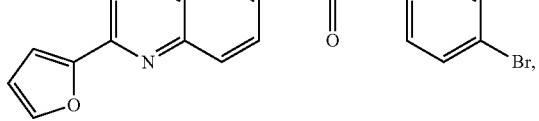
-continued
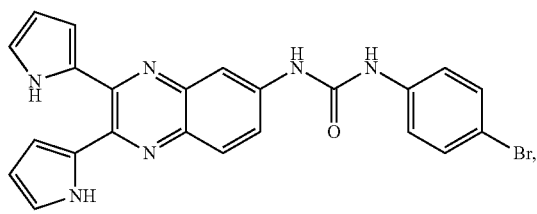
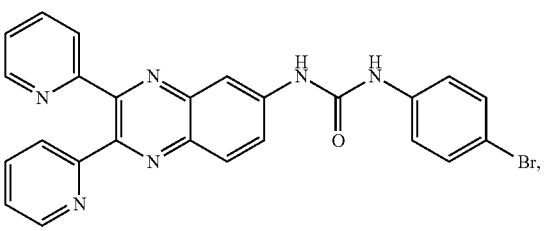
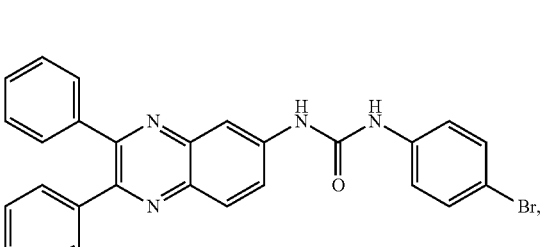
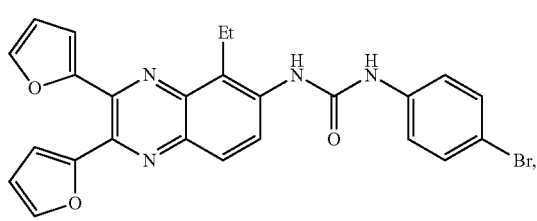
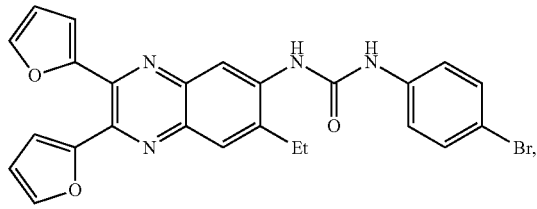
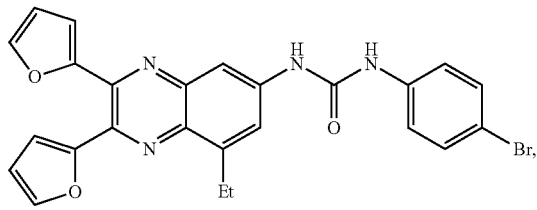
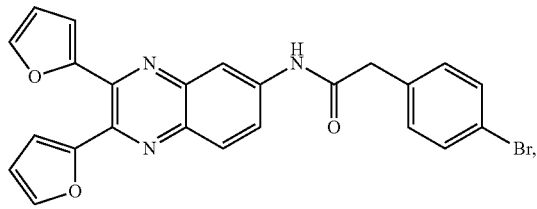

-continued
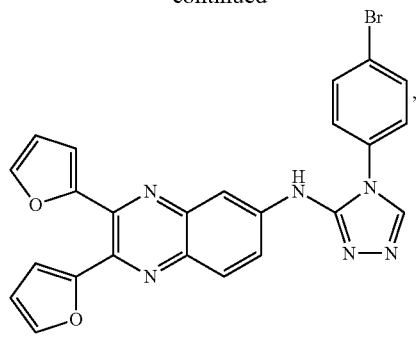
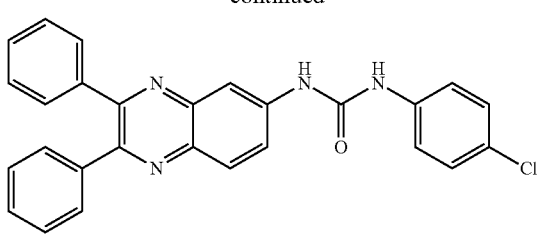
or a salt thereof.
17. A compound having a structure selected from:
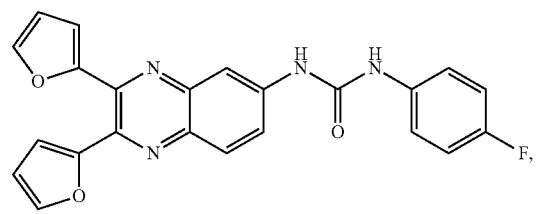 [SMILES: O=C(Nc1ccc(Br)cc1)Nc1ccc2nc(-c3ccco3)c(-c3ccco3)nc2c1]
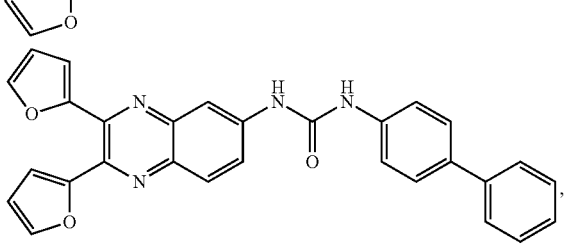
or a salt thereof.
18. A compound having a structure selected from:
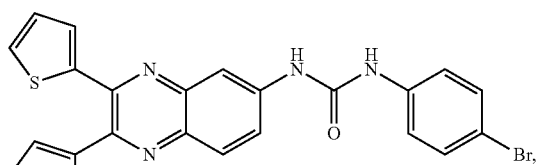
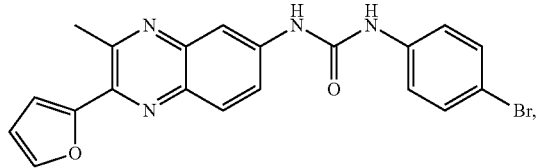

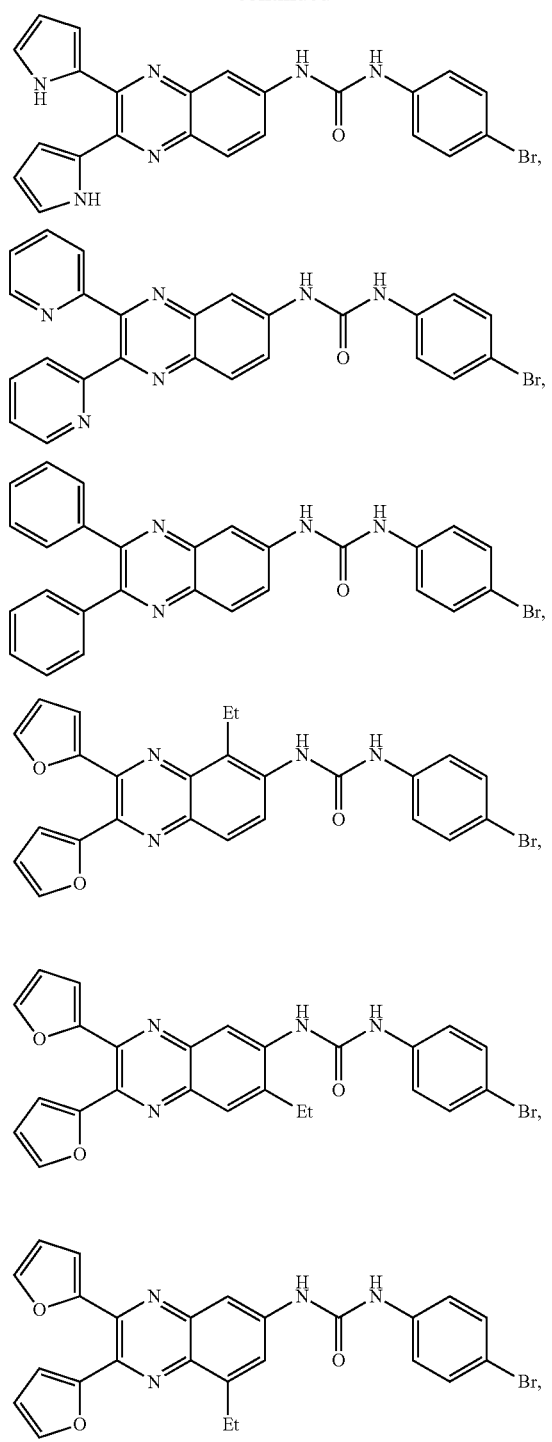
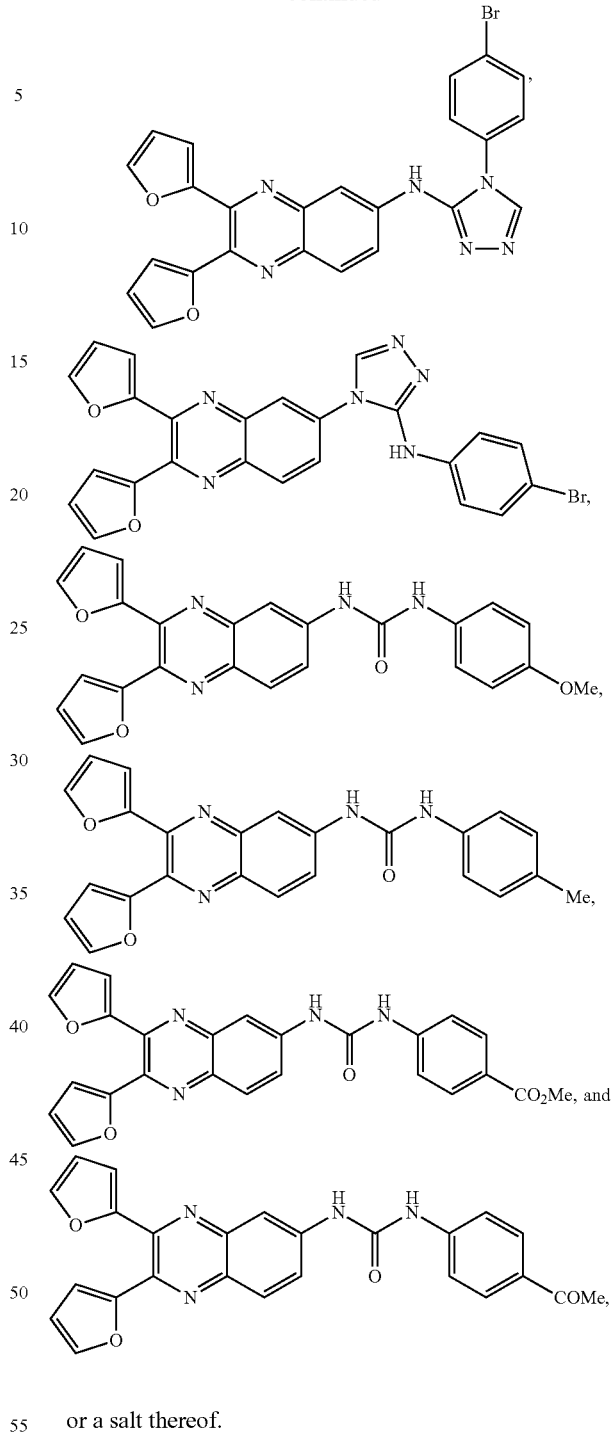
or a salt thereof.
19. A compound having a structure selected from:
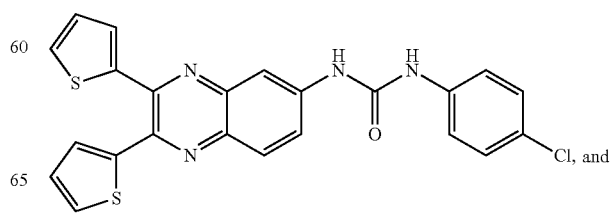

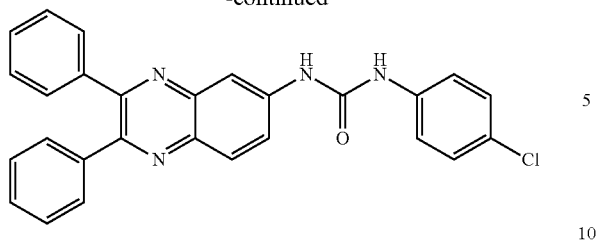
or a salt thereof.
20. A compound having a structure:
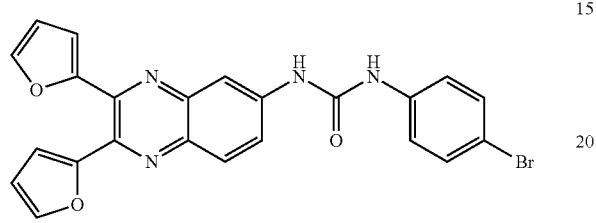
or a salt thereof.